US012807975B2

(12) United States Patent
Hong et al.

(10) Patent No.: US 12,807,975 B2
(45) Date of Patent: Nov. 24, 2026

(54) METHOD FOR SYNTHESIZING A FLUORINE-CONTAINING CHIRAL AMINE COMPOUND

(71) Applicant: ASYMCHEM LABORATORIES (TIANJIN) CO., LTD., Tianjin (CN)

(72) Inventors: Hao Hong, Morrisville, NC (US); Gage James, Morrisville, NC (US); Yi Xiao, Tianjin (CN); Na Zhang, Tianjin (CN); Xiang Li, Tianjin (CN); Xiangjun Jiang, Tianjin (CN); Shunxing Lv, Tianjin (CN)

(73) Assignee: ASYMCHEM LABORATORIES (TIANJIN) CO., LTD., Tianjin (CN)

( * ) Notice: Subject to any disclaimer, the term of this patent is extended or adjusted under 35 U.S.C. 154(b) by 830 days.

(21) Appl. No.: 17/904,994

(22) PCT Filed: Mar. 31, 2020

(86) PCT No.: PCT/CN2020/082595
§ 371 (c)(1),
(2) Date: Aug. 25, 2022

(87) PCT Pub. No.: WO2021/168988
PCT Pub. Date: Sep. 2, 2021

(65) Prior Publication Data

US 2024/0294954 A1 Sep. 5, 2024

(30) Foreign Application Priority Data

Feb. 26, 2020 (CN) ......................... 202010118880.8

(51) Int. Cl.

| | |
|---|---|
| ***C12N 9/10*** | (2006.01) |
| ***C12P 13/00*** | (2006.01) |
| ***C12P 13/02*** | (2006.01) |
| ***C12P 17/04*** | (2006.01) |
| ***C12P 17/10*** | (2006.01) |
| ***C12P 17/12*** | (2006.01) |

(52) U.S. Cl.
CPC ............. *C12P 13/001* (2013.01); *C12P 13/02* (2013.01); *C12P 17/04* (2013.01); *C12P 17/10* (2013.01); *C12P 17/12* (2013.01)

(58) Field of Classification Search
None
See application file for complete search history.

(56) References Cited

FOREIGN PATENT DOCUMENTS

| | | | |
|---|---|---|---|
| CN | 108048419 | A | 5/2018 |
| CN | 108384767 | A | 8/2018 |
| CN | 110592042 | | 12/2019 |
| EP | 3415630 | A1 | 12/2018 |
| WO | 2019011236 | A1 | 1/2019 |
| WO | 2019095161 | A1 | 5/2019 |
| WO | 2019148494 | A1 | 8/2019 |

OTHER PUBLICATIONS

Singh et al. (Curr. Protein Pept. Sci. 18:1-11, 2014.*
Zhang et al. (Structure 26:1474-1485, 2018.*
International Search Report for Application No. PCT/CN2020/082595, mailed Jun. 29, 2020, 2 Pages.
Xie, et al., “Generalized access to fluorinated B-keto amino compounds through asymmetric additions of a,a-difluoroenolates to CF3-sulfinylimine”, Organic and Biomolecular Chemistry, vol. 12, pp. 7836-7843. (2014).
Extended European Search Report for European Patent Application No. 20922355.1, dated Aug. 24, 2023, 10 Pages.
Holzer, A. K., et al., “Asymmetric Biocatalytic Amination of Ketones at the Expense of NH3 and Molecular Hydrogen,” Organic Letters, vol. 17 (2015), pp. 2431-2433.

* cited by examiner

*Primary Examiner* — Richard G Hutson
(74) *Attorney, Agent, or Firm* — Riverside Law LLP

(57) ABSTRACT

The present invention provides a method for synthesizing a fluorine-containing chiral amine compound. The method comprised: reacting an amino donor with a fluorine-containing dihydroxy ketal compound under a catalysis of a transaminase to generate the fluorine-containing chiral amine compound, wherein the transaminase is derived from a plurality of strains. The transaminase of the present application has substrate specificity on the fluorine-containing dihydroxy ketal compound, and may effectively catalyze this type of the substrate to be converted into the fluorine-containing chiral amine compound. In addition, the transaminase has catalytic activity on a plurality of the fluorine-containing dihydroxy ketal compounds, and is relatively high in reaction selectivity and activity. The method catalyzed by the bio-enzyme is not only short in route, but also high in product yield, and the production using the method reduces cost, organic solvents and three wastes.

13 Claims, 4 Drawing Sheets

Specification includes a Sequence Listing.

METHOD FOR SYNTHESIZING A FLUORINE-CONTAINING CHIRAL AMINE COMPOUND

CROSS-REFERENCE TO RELATED APPLICATIONS

This application is a national phase application filed under 35 U.S.C. § 371 claiming benefit to International Patent Application No. PCT/CN2020/082595, filed Mar. 31, 2020, which claims the benefit of priority from Chinese Patent Application No. 202010118880.8, filed Feb. 26, 2020, each of which is hereby incorporated by reference in its entirety herein.

REFERENCE TO A "SEQUENCE LISTING," A TABLE, OR A COMPUTER PROGRAM LISTING APPENDIX SUBMITTED AS AN ASCII TEXT FILE

The present application hereby incorporates by reference the entire contents of the text file named "PN183071_SequenceListing.txt." The file containing the Sequence Listing of the present application was created on Mar. 17, 2026, and is 91,190 bytes in size.

TECHNICAL FIELD

The present invention relates to the field of synthesis of fluorine-containing compounds, in particular to a method for synthesizing a fluorine-containing chiral amine compound.

BACKGROUND

Fluorine-containing compounds are a very important type of compounds in medicine and agricultural chemistry. In the past decade, fluoride-containing drugs are grown at an unprecedented rate. Therefore, the development of a green and efficient synthesis method plays a crucial role. Fluorine-containing dihydroxy ketal compounds are also one of this type of the compounds

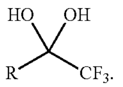

Important fluorine-containing chiral amine compounds

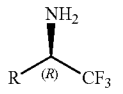

and

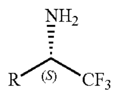

may be synthesized by this type of substrates. At present, methods for synthesizing fluorine-containing chiral amines by fluorine-containing dihydroxy ketal are mainly as follows.

1. According to a reaction route shown in a Formula 1: under an alkaline condition, a C—C bond of a fluorine-containing dihydroxy ketal compound 1 is easily cleaved, to form a trifluoroacetic acid and a corresponding fluorine-containing enol compound 2. A compound 3 is used as a Mannich reaction acceptor, a compound 4 is obtained after a Mannich reaction, and then a sulfinyl group is removed to obtain a target product, a fluorine-containing chiral amine compound.

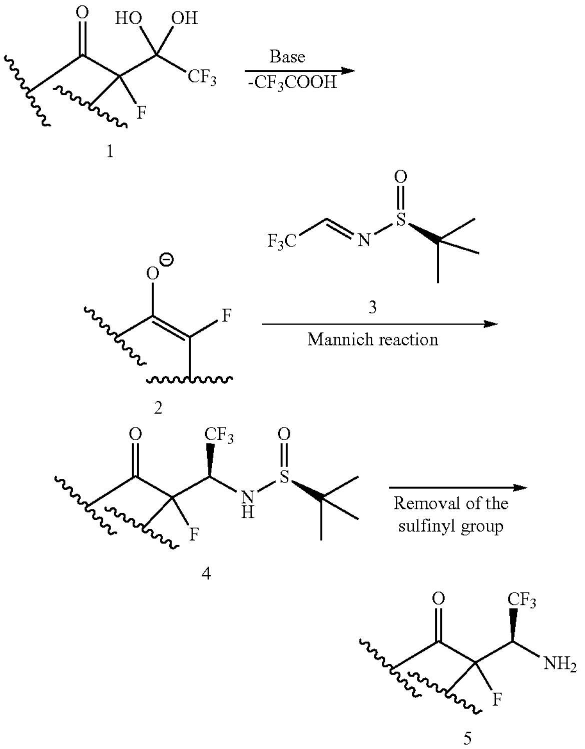

2. According to a reaction route shown in a Formula 2: a fluorine-containing dihydroxy ketal compound 6 is reacted with a benzylamine compound, a chiral amino group is introduced, and then a benzyl group is removed to obtain a target compound 8.

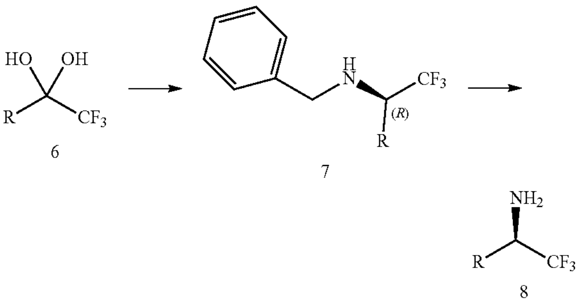

The substrate of the route shown in the above the Formula 1 has limitations, and the target product may be obtained after a three-step reaction, and the yield is low. The reaction route is longer, and chemical reagents used in the reaction produce a large amount of three wastes. The route shown in the Formula 2 is a two-step reaction, but the reaction sometimes requires the use of expensive metal ligands or catalysts, as well as the use of highly toxic compounds. Similarly, the use of chemical reagents in the reaction produces a large amount of the three wastes.

Therefore, there is still a need to provide a new synthesis method for such fluorine-containing dihydroxy ketal compounds.

SUMMARY

A main purpose of the present invention is to provide a method for synthesizing a fluorine-containing chiral amine compound, as to solve a problem in an existing technology that the fluorine-containing chiral amine compound is long in synthesis route.

In order to achieve the above purpose, the present invention provides a method for synthesizing a fluorine-containing chiral amine compound, wherein the method comprises: reacting an amino donor with a fluorine-containing dihydroxy ketal compound under the catalysis of a transaminase to generate the fluorine-containing chiral amine compound, wherein the transaminase is derived from *Chromobacterium violaceum* DSM30191 (CVTA)(NCBI Reference Sequence: WP_011135573.1). *Fonsecaea pedrosoi* CBS 271.37 (NCBI Reference Sequence: XP_013286281.1), *Klebsiella pneumoniae* subsp. *pneumoniae* Ecl8 (GenBank: CCN29541.1), *Mycobacterium* goodie (GenBank: AKS36000.1), *Paracoccus denitrificans*(NCBI Reference Sequence: WP_011746975.1), *Penicillium brasilianum*(GenBank: CEJ55334.1), *Enterobacter* sp.TL3 (NCBI Reference Sequence: WP_014885677.1), *Aspergillus terreus* NIH2624 (NCBI Reference Sequence: XP_001209325.1), *Exophiala spinifera*(NCBI Reference Sequence: XP_016233821.1), *Deinococcus geothermalis* (strain DSM 11300)(NCBI Reference Sequence: WP_011530545.1), *Geomyces destructans* 20631-21 (GdTA) in *E. coli*(GenBank: ELR05573.1), *Pseudomonas putida* KT2440 (NCBI Reference Sequence: WP_010954554.1), *Lysinibacillus sphaericus*(NCBI Reference Sequence: WP_024363741.1), *Bacillus* megaterium-DSM 319 (NCBI Reference Sequence: WP_013082219.1), *Trichoderma harzianurn*(GenBank: KKP07030.1), *Aspergillus fumigatus* R-ATAs (AspFum)(NCBI Reference Sequence: XP_748821.1), *Geobacillus thermodenitrificans* subsp. *thermodenitrificans* DSM 465 (NCBI Reference Sequence: WP_008879436.1). *Cladophialophora bantiana* CBS 173.52 (NCBI Reference Sequence: XP_016617948.1), *Bacillus megaterium*(NCBI Reference Sequence: WP_016763026.1), *Burkholderia thailandensis* MSMB121 (BtS-TA)(GenBank: AGK49399.1), *Klebsiella pneumoniae* subsp. *pneumoniae* MGH 78578 (NCBI Reference Sequence: WP_002920226.1), *Geobacillus toebii* (NCBI Reference Sequence: WP_062753894.1) and *Talaromyces cellulolyticus*(GenBank: GAM37533.1).

Further, the transaminase has an amino acid sequence shown in SEQ ID NO: 1, SEQ ID NO: 2, SEQ ID NO: 3 or SEQ ID NO: 4.

Further, the fluorine-containing dihydroxy ketal compound has a structural as shown in formula I:

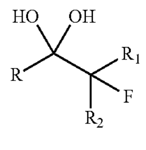

Herein, R is selected from an alkyl, a cycloalkyl, an aryl, alkyl containing one or more heteroatoms, a cycloalkyl containing one or more heteroatoms, an aryl containing one or more heteroatoms, an amide compound residue or an ether compound residue, and R1 and R2 are the same or different hydrogen atoms or halogen atoms.

More preferably, the fluorine-containing dihydroxy ketal compound has a structural as shown in formula II

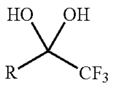

Further, the fluorine-containing dihydroxy ketal compound is selected from any one of the followings.

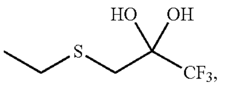
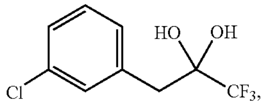
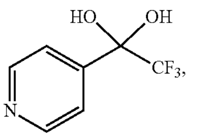
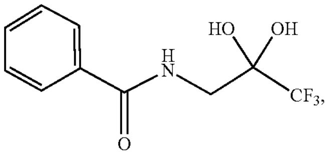
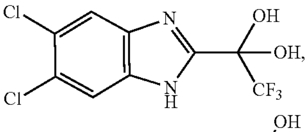
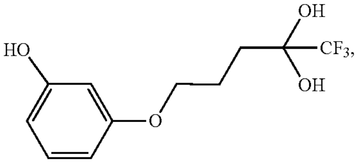
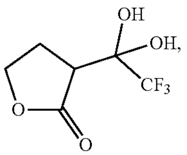
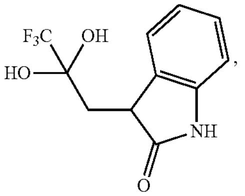
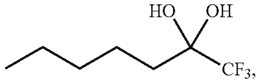
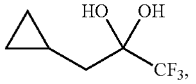
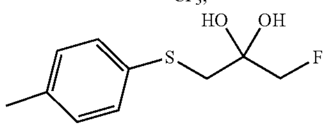

and

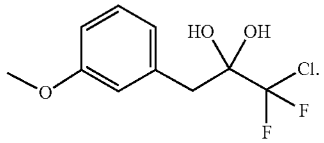

Further, the method includes: mixing a phosphate buffer with the amino donor to obtain a first mixed solution, adding the fluorine-containing dihydroxy ketal compound to the first mixed solution to obtain a second mixed solution; adding the transaminase to the second mixed solution to obtain a reaction mixture; and isolating the fluorine-containing chiral amine compound from the reaction mixture.

Further, before adding the fluorine-containing dihydroxy ketal compound to the first mixed solution, the method further includes: adjusting a pH value of the first mixed solution to 7.0-9.0; and preferably, adding the transaminase to the second mixed solution, and adjusting pH of the second mixed solution after adding the transaminase to 7.0-9.0, to obtain the reaction mixture.

Further, isolating the fluorine-containing chiral amine compound from the reaction mixture comprises: adjust the acidity of the reaction mixture to obtain a denatured transaminase, and preferably adjusting a pH value of the reaction mixture to 1-2; filtering and removing the denatured transaminase, to obtain filtrate; extracting the filtrate, to obtain the fluorine-containing chiral amine compound; preferably, the filtering is carried out with dichloromethane; and preferably, the extracting is carried out with the dichloromethane.

Further, the extraction is carried out 2~5 times, and after the extractions, a step of drying organic phase resulting from the extractions is further included. Preferably, combining the organic phases obtained from the extractions to obtain an extract; drying the extract to obtain a dried organic phase of product; and concentrating the dried organic phase of product to no fraction under a temperature less than 35 °C and a pressure no more than −0.06 Mpa to obtain the fluorine-containing chiral amine compound.

Further, a mass ratio of the transaminase to the fluorine-containing dihydroxy ketal compound is 0.4: 1-1.0:1.

Further, a concentration of the fluorine-containing dihydroxy ketal compound is 60 g/L~100 g/L.

Further, the amino donor is selected from isopropylamine, a hydrochloride of the isopropylamine, alanine, aniline or n-butylamine.

A technical scheme of the present invention is applied, the transaminase of the present application has substrate specificity on the fluorine-containing dihydroxy ketal compound, and may effectively catalyze this type of the substrate to be converted into the fluorine-containing chiral amine compound. In addition, the transaminase has catalytic activity on a plurality of the fluorine-containing dihydroxy ketal compounds, and is relatively high in reaction selectivity and activity. The method catalyzed by the bio-enzyme is not only short in route, but also high in product yield, and the production using the method reduces cost, organic solvents and three wastes.

BRIEF DESCRIPTION OF THE DRAWINGS

Drawings of the description constituting a part of the present application are used to provide further understanding of the present invention, and exemplary embodiments of the present invention and descriptions thereof are used to explain the present invention, and do not constitute improper limitation to the present invention. In the drawings.

DETAILED DESCRIPTION OF THE EMBODIMENTS

Figure 1:
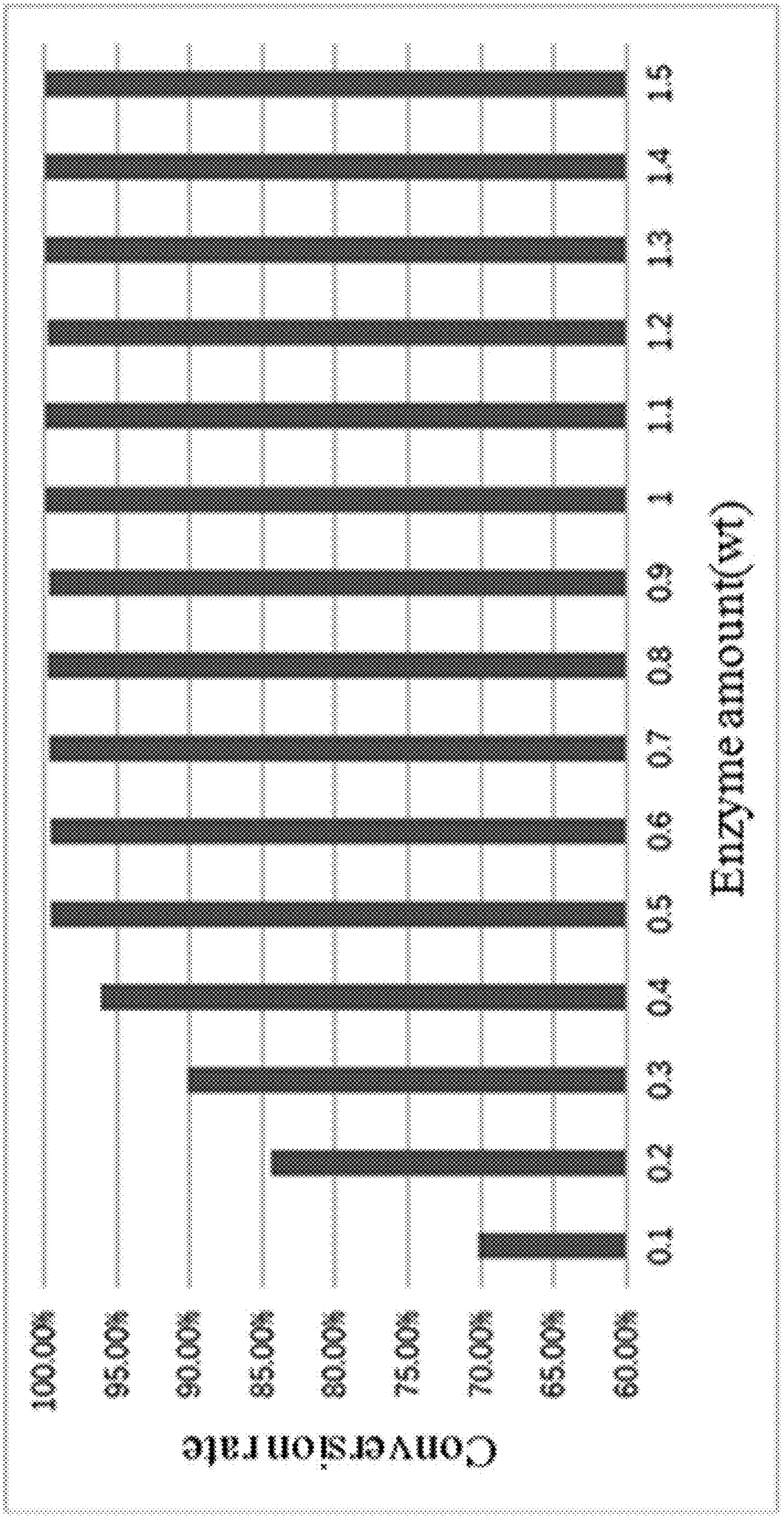
FIG. 1 shows effects of different enzyme amounts on the conversion rate of the same amount of a substrate in Embodiment 13 of the present invention.

It should be noted that embodiments in the present application and features of the embodiments may be combined with each other in the case without conflicting. The present invention is described in detail below in combination with the embodiments.

As mentioned in the background, in an existing technology, while the fluorine-containing dihydroxy ketal compound is used as a starting raw material to synthesize the fluorine-containing chiral amine compound, there is not only a defect of a long reaction route, but also a problem of three industrial wastes. In order to improve this situation, the inventor of the present application tries to improve an existing synthesis route from the perspective of high efficiency and environmental protection. In the research process, it is found by the inventor that a transaminase developed by the applicant himself not only has the general catalytic activity of the transaminase for catalyzing ketone compounds with a pyridoxal phosphate (PLP) as a coenzyme, but also has the activity of catalyzing the fluorine-containing dihydroxy ketal compound. In addition, it is found from the further research that while the transaminase is used to catalyze a fluorine-containing dihydroxy ketal compound substrate, not only a target product may be obtained by an one-step reaction, but also the substrate type is wide. Due to the high selectivity of a biotransformation reaction using the transaminase, an enantiomeric excess (ee) value of the target product is greatly improved. Moreover, the use of a biological enzyme to catalyze the reaction greatly improves the production efficiency and reduces the generation of organic solvents and three wastes.

On the basis of the above research results, the applicant proposes a technical scheme of the present application. In a typical embodiment of the present application, a method for synthesizing a fluorine-containing chiral amine compound is provided, and the method includes: reacting an amino donor with a fluorine-containing dihydroxy ketal compound under a catalysis of a transaminase to generate the fluorine-containing chiral amine compound, herein the transaminase is derived from *Chromobacterium violaceum* DSM30191 (CVTA)(NCBI Reference Sequence: WP_011135573.1), *Fonsecaea pedrosoi* CBS 271.37 (NCBI Reference Sequence: XP_013286281.1), *Klebsiella pneunoniae* subsp. *pneumoniae* Ecl8 (GenBank: CCN29541.1), *Mycobacterium goodii* (GenBank: AKS36000.1), *Paracoccus denitrificans*(NCBI Reference Sequence: WP_011746975.1), *Penicillium brasilianum*(GenBank: CEJ55334.1). *Enterobacter* sp.TL3 (NCBI Reference Sequence: WP_014885677.1). *Aspergillus terreus* NIH2624 (NCBI Reference Sequence: XP_001209325.1), *Exophiala spinifera*(NCBI Reference Sequence: XP_016233821.1), *Deinococcus geothermalis* (strain DSM 11300)(NCBI Reference Sequence: WP_011530545.1), *Ceomyces destructans* 20631-21 (GdTA) in *E. coli*(GenBank: ELR05573.1), *Pseudomonas putida* KT2440 (NCBI Reference Sequence: WP_010954554.1), *Lysinibacillus sphaericus* (NCBI Reference Sequence: WP_024363741.1), *Bacillus megaterium* DSM 319 (NCBI Reference Sequence: WP_013082219.1), *Trichoderma harzianurn* (GenBank: KKP07030.1), *Aspergillus fumigatus* R-ATAs (AspFum)(NCBI Reference Sequence: XP_748821.1). *Geobacillus thermodenitrificans* subsp. *thermodenitrificans* DSM 465 (NCBI Reference Sequence: WP_008879436.1). *Cladophialophora bantiana* CBS 173.52 (NCBI Reference Sequence: XP_016617948.1), *Bacillus megaterium*(NCBI Reference Sequence: WP_016763026.1), *Burkholderia thailandensis* MSMB121 (BtS-TA)(GenBank: AGK49399.1), *Klebsiella pneurmoniae* subsp. *pneumoniae* MGH 78578 (NCBI Reference Sequence: WP_002920226.1), *Geobacillus toebii* (NCBI Reference Sequence: WP_062753894.1) and *Talaromyces cellulolyticus*(GenBank: GAM37533.1).

The sequences of the above transaminases are shown in Table 1 below.

TABLE 1

| | SEQ ID NO: |
|---|---|
| WP_011135573.1 | 5 |
| XP_013286281.1 | 6 |
| CCN29541.1 | 7 |
| AKS36000.1 | 8 |
| WP_011746975.1 | 9 |
| CEJ55334.1 | 10 |
| WP_014885677.1 | 11 |
| XP_001209325.1 | 12 |
| XP_016233821.1 | 13 |
| WP_011530545.1 | 14 |
| ELR05573.1 | 15 |
| WP_010954554.1 | 16 |
| WP_024363741.1 | 17 |
| WP_013082219.1 | 18 |
| KKP07030.1 | 19 |
| XP_748821.1 | 20 |
| WP_008879436.1 | 21 |
| XP_016617948.1 | 22 |
| WP_016763026.1 | 23 |
| AGK49399.1 | 24 |
| WP_002920226.1 | 25 |
| WP_062753894.1 | 26 |
| GAM37533.1 | 27 |

More preferably, the transaminase has an amino acid sequence shown below in SEQ ID NO: 1, SEQ ID NO: 2, SEQ ID NO: 3 or SEQ ID NO: 4:

(SEQ ID NO: 1)

MQKQRTCSQWRELDAAHHLHPFTDTASLNQAGARVMTRGEGVYLWDCEG

NKIIDGMAGLWCVNVGYGRKDFAEAARRQMEELPFYNTFYKTTHPAVVE

LSSLLAEVTPAGFDRVFYTNSGSESVDTMIRMVRRYWDVQGKPEKKTLI

GRWWGYHGSTIGGASLGGFKYMHEQGDLPIPGMAHIEQPWWYKHGKDMT

PDEFGVVAARWLEEKILEIGADKVAAFVGEPIQGAGGVIVPPATYWPEI

ERICRKYDVLLVADEVICGFGRTGEWFGHQHFGFQPDLFTAAKGLSSGY

LPIGAVFVGKRVAEGLIAGGDFNHGFTYSGHPVCAAVAHANVAALRDEG

IVQRVKDDIGPYMQKRWRETFSRFEHVDDVRGVGMLLAFTLVKNKAKRE

LFPDFGEIGTLCRDIFFRNNLIMDSCGDHIVCAPPLVMTRAEVDEMLAV

AERCLEEFEQTLKARGLA.

(SEQ ID NO: 2)

MQKQRTCSQWRELDAAHHLHPFTDTASLNQAGARVMTRGEGVYLWDCEG

NKIIDGMAGLWCVNVGYGRKDFAEAARRQMEELPFYNTFYKTTHPAVVE

LSSLLAEVTPAGFDRVFYTNSGSESVDTMIRMVRRYWDVQGKPEKKTLI

GRWWGYHGSTIGGASLGGFKYMHEQGDLPIPGMAHIEQPWWYKHGKDMT

PDEFGVVAARWLEEKILEIGADKVAAFVGEPIQGAGGVIVPPATYWPEI

ERICRKYDVLLVADEVICGFGRTGEWFGHQHFGFQPDLFTAAKGLSSGY

LPIGAVFVGKRVAEGLIAGGDFNHGFTYSGHPVCAAVAHANVAALRDEG

-continued

IVQRVKDDIGPYMQKRWRETFSRFEHVDDVRGVGMLLAFTLVKNKAKRE

LFPDFGEIGTLCRDIFFRNNLIMDSCGDHIVAAPPLVMTRAEVDEMLAV

AERCLEEFEQTLKARGLA.

(SEQ ID NO: 3)

MQKQRTCSQWRELDAAHHLHPFTDTASLNQAGARVMTRGEGVYLWDCEG

NKIIDGMAGLWCVNVGYGRKDFAEAARRQMEELPFYNTFYKTTHPAVVE

LSSLLAEVTPAGFDRVFYTNSGSESVDTMIRMVRRYWDVQGKPEKKTLI

GRWWGYHGSTIGGASLGGFKYMHEQGDLPIPGMAHIEQPWWYKHGKDMT

PDEFGVVAARWLEEKILEIGADKVAAFVGEPIQGAGGVIVPPATYWPEI

ERICRKYDVLLVADEVICGFGRTGEWFGHQHFGFQPDLFTAAKGLSSGY

LPIGAVFVGKRVAEGLIAGGDFNHGFTYSGHPVCAAVAHANVAALRDEG

IVQRVKDDIGPYMQKRWRETFSRFEHVDDVRGVGMLLAFTLVKNKAKRE

LFPDFGEIGTLCRDIFQRNNLIMDSCGDHIVSAPPLVMTRAEVDEMLAV

AERCLEEFEQTLKARGLA.

(SEQ ID NO: 4)

MQKQRTCSQWRELDAAHHLHPFTDTASLNQAGARVMTRGEGVYLWDCEG

NKIIDGMAGLWCVNVGYGRKDFAEAARRQMEELPFYNTFYKTTHPAVVE

LSSLLAEVTPAGFDRVFYTNSGSESVDTMIRMVRRYWDVQGKPEKKTLI

GRWWGYHGSTIGGASLGGFKYMHEQGDLPIPGMAHIEQPWWYKHGKDMT

PDEFGVVAARWLEEKILEIGADKVAAFVGEPIQGAGGVIVPPATYWPEI

ERICRKYDVLLVADEVICGFGRTGEWFGHQHFGFQPDLFTAAKGLSSGY

LPIGAVFVGKRVAEGLIAGGDFNHGFTYSGHPVCAAVAHANVAALRDEG

IVQRVKDDIGPYMQKRWRETFSRFEHVDDVRGVGMLLAFTLVKNKAKRE

LFPDFGEIGTLCRDIFHRNNLIMDSCGDHIVSAPPLVMTRAEVDEMLAV

AERCLEEFEQTLKARGLA.

As described above, the above transaminase of the present application has substrate specificity on the fluorine-containing dihydroxy ketal compound, and may effectively catalyze this type of the substrate to be converted into the fluorine-containing chiral amine compound. In addition, the transaminase has catalytic activity on a plurality of the fluorine-containing dihydroxy ketal compounds, and also has relatively high reaction selectivity and activity. The bio-enzyme catalytic synthesis method is not only short in route, but also high in product yield, the production cost is greatly reduced, and the production of organic solvents and three wastes is reduced.

The transaminase shown in any one of the above SEQ ID NO: 1 to 4 is a ω-transaminase, and all are derived from *Chromobacterium violaceum* DSM30191 (CVTA). It is separated from *Chromobacterium violaceum* DSM30191 (CVTA) according to an existing method.

In a preferred embodiment, the fluorine-containing dihydroxy ketal compound has a structure shown in the following formula I:

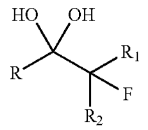

Herein, R is selected from an alkyl, a cycloalkyl, an aryl, an alkyl containing one or more heteroatoms, a cycloalkyl containing one or more heteroatoms, an aryl containing one or more heteroatoms, an amide compound residue or an ether compound residue, and R1 and R2 are the same or different hydrogen or halogen atoms.

In a more preferred embodiment, both R1 and R2 are fluorine, namely the fluorine-containing dihydroxy ketal compound has a structure shown in the following structural formula II:

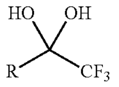

In a preferred embodiment, the fluorine-containing dihydroxy ketal compound is selected from any one of the followings.

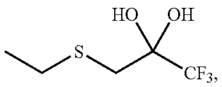

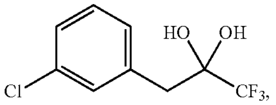

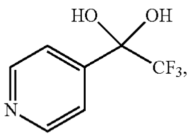

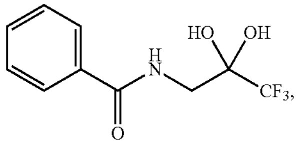

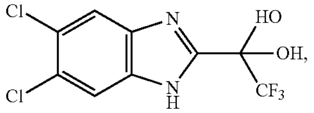

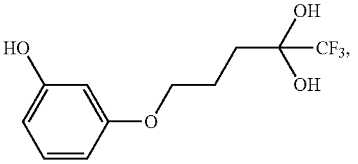

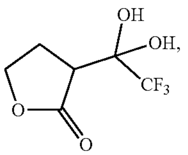

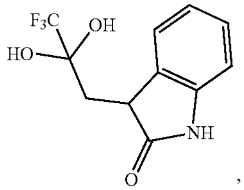

,

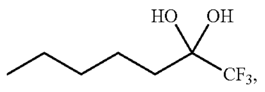

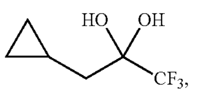

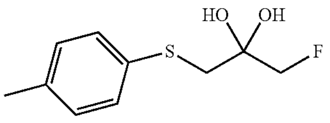

and

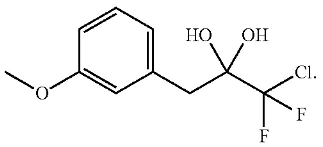

The transaminase of the present application has the catalytic activity for the above fluorine-containing dihydroxy ketal compound.

A specific step of using the transaminase of the present application to catalyze a transamination reaction of the fluorine-containing dihydroxy ketal compound is similar to an existing transamination reaction. In a preferred embodiment, the method includes: mixing a phosphate buffer with the amino donor, to obtain a first mixed solution. Adding the fluorine-containing dihydroxy ketal compound to the first mixed solution, to obtain a second mixed solution, Adding the transaminase to the second mixed solution, to obtain a reaction mixture. And isolating the fluorine-containing chiral amine compound from the reaction mixture.

The synthesis method reduces the reaction volume by the above step-by-step reaction (a previous material may be changed in order, and the last addition of the transaminase is to ensure that the reaction is performed immediately after the addition, to prevent the inactivation of the transaminase due to a longer time of other operations), so that the transaminase is relatively high in catalytic activity and efficiency on the substrate, thereby the higher product yield is obtained, and the production efficiency is improved.

In a preferred embodiment, before adding the fluorine-containing dihydroxy ketal compound to the first mixed solution, the method further comprises: adjusting a pH value of the first mixed solution to 7.0-9.0; and preferably, adding the transaminase to the second mixed solution, and adjusting pH of the second mixed solution after adding the transaminase to 7.0-9.0, to obtain the reaction mixture.

In the above preferred embodiment, before adding the fluorine-containing dihydroxy ketal compound to the first mixed solution, the pH value of the first mixed solution is adjusted. Its purpose is to adjust to the optimum pH of the enzyme reaction before adding the enzyme, and prevent the inactivation of the enzyme in the adding process. After the transaminase is added to the second mixed solution, the pH value of the system is also adjusted, its function is to ensure that the reaction is performed at the optimum pH. It is better to keep the same range of pH value adjustment for the above two times, for example, the pH value is previously adjusted to 7.8, and it is also adjusted to 7.8 after the transaminase is added.

The above step of separating, which obtains the target product from the mixed solution after the reaction, may be performed by using a known separation and purification method. In a preferred embodiment, wherein isolating the fluorine-containing chiral amine compound from the reaction mixture comprises: adjust the acidity of the reaction mixture to denature the transaminase, and preferably adjusting a pH value of the reaction mixture to 1-2; filtering and removing the denatured transaminase, to obtain a filtrate; extracting the filtrate, to obtain the fluorine-containing chiral amine compound; preferably, filtering is carried out with dichloromethane; and preferably, extracting is carried out with the dichloromethane.

A mode of adjusting the acidity is used to denature a reacted enzyme protein. Compared with other denaturation modes (such as high temperature, alkali adjustment or salting out), it has advantages that the denaturation is more thorough, most of products are stable under an acidic condition, and a subsequent operation may directly extract other impurities in the system under the acidic condition. The extraction with the dichloromethane has the advantage of higher extraction efficiency compared to the extraction with other extraction solvents (such as ethyl acetate, methyl tert-butyl ether, or isopropyl acetate).

In order to further improve the purity and yield, in a preferred embodiment, the extraction is carried out 2~5 times, and after the extraction, a step of drying organic phase is further included. Preferably, combining the organic phases obtained from the extractions to obtain an extract; drying the extract to obtain a dried organic phase of product; concentrating the dried organic phase of product to no fraction under a temperature less than 35 °C and a pressure no matter than −0.06 Mpa to obtain the fluorine-containing chiral amine compound (a purpose of drying is to reduce the water content in the product, and the pressure affects the concentration rate).

In a preferred embodiment, the mass ratio of the transaminase to the fluorine-containing dihydroxy ketal compound is 0.4:1~1.0:1, and the conversion rate of the substrate under this mass ratio reaches more than 95%.

In a preferred embodiment, the concentration of the fluorine-containing dihydroxy ketal compound is 60 g/L~100 g/L. In this concentration range, the use of the biological enzyme for the reaction not only increase the conversion rate of the substrate to 99%, but also helps to improve the concentration of the substrate, thereby the production efficiency is improved, and the generation of organic solvents and three wastes is reduced.

In a preferred embodiment, the amino donor is selected from isopropylamine, hydrochloride of the isopropylamine, alanine, aniline or n-butylamine. The conversion rates of the above amino-donating substrates may all reach more than 90%.

The beneficial effects of the present application are further described below in combination with specific embodiments. It should be noted that the room temperature in the following embodiments refers to a temperature within the normal temperature range of 10~25 °C, and the transaminase used in the following Embodiments 1 to 15 is the transaminase shown in SEQ ID NO: 4.

Embodiment 1

50 mL of 100 mmol/L phosphate buffer (5 vol) and 32 mL of 5 mol/L isopropylamine hydrochloride solution (3.2 vol, 3 eq) are added to a 250 mL four-neck flask at the room temperature, and it is adjusted that pH=7.5~8.0. Then 0.1 g of pyridoxal phosphate (1 wt %), and 10 g of

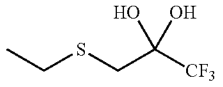

are added, and stirred uniformly, then 10 ml of transaminase enzyme solution (0.5 wt, 0.5 g/ml) is added, and adjust the pH to 7.5~8.0. The temperature is raised to 29 °C and it is stirred and reacted overnight. After the reaction is completed, the system is adjusted to pH=1, as to denature a protein. After being filtered, filtrate is extracted with 50 mL of dichloromethane. Aqueous phase is adjusted to pH=13, and extracted for three times with 50 ml of dichloromethane. Organic phases are combined and dried with an anhydrous magnesium sulfate, then the organic phase is concentrated until there is no fraction under conditions of T<35 °C and P≤−0.06 Mpa. A target product

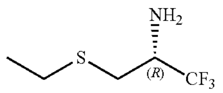

is obtained.

It is detected by a high performance liquid chromatography (HPLC), purity: 98%, ee value: 100%, yield: 87%.

Embodiment 2

50 mL of 100 mmol/L phosphate buffer (5 vol) and 25 mL of 5 mol/L isopropylamine hydrochloride solution (2.5 vol, 3 eq) are added to a 250 mL four-neck flask at the room temperature, and it is adjusted that pH=8.0~8.5. Then 0.1 g of pyridoxal phosphate (1 wt %), and 10 g of

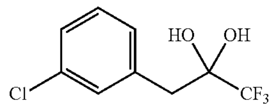

are added, and stirred uniformly, then 10 ml of transaminase enzyme solution (0.5 wt, 0.5 g/ml), and adjust the pH to 8.0~8.5. The temperature is raised to 20 °C and it is stirred and reacted overnight. After the reaction is completed, the system is adjusted to pH=2, as to denature a protein. After being filtered, filtrate is extracted with 50 mL of dichloromethane. Aqueous phase is adjusted to pH=13, and extracted for three times with 50 ml of ethyl acetate. Organic phases are combined and dried with an anhydrous magnesium sulfate, then the organic phase is concentrated until there is no fraction under conditions of T<45 °C and P≤−0.08 Mpa. A target product

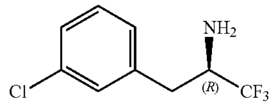

is obtained.

It is detected by HPLC, purity: 99%, ee value: 100%, yield: 86%.

Embodiment 3

50 mL of 100 mmol/L phosphate buffer (5 vol) and 31 mL of 5 mol/L isopropylamine hydrochloride solution (3.1 vol, 3 eq) are added to a 250 mL four-neck flask at the room temperature, and it is adjusted that pH=7.0~7.5. Then 0.1 g of pyridoxal phosphate (1 wt %), and 10 g of

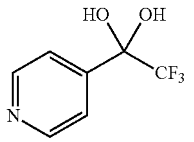 [SMILES: OC(O)(c1ccncc1)C(F)(F)F]

are added, and stirred uniformly, then 10 ml of transaminase enzyme solution (0.5 wt, 0.5 g/ml) is added. The temperature is raised to 45~50 °C and it is stirred and reacted overnight. After the reaction is completed, the system is adjusted to pH=1, as to denature a protein. After being filtered, filtrate is extracted with 50 mL of dichloromethane. Aqueous phase is adjusted to pH=12, and extracted for three times with 50 ml of dichloromethane. Organic phases are combined and dried with an anhydrous magnesium sulfate, then the organic phase is concentrated until there is no fraction under conditions of T<35 °C and P≤−0.06 Mpa. A target product

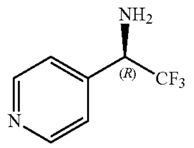

is obtained.

It is detected by HPLC, purity: 97%, ee value: 100%, yield: 83%.

Embodiment 4

50 mL of 100 mmol/L phosphate buffer (5 vol) and 24 mL of 5 mol/L isopropylamine hydrochloride solution (2.4 vol, 3 eq) are added to a 250 mL four-neck flask at the room temperature, and it is adjusted that pH=8.5~9.0. Then 0.1 g of pyridoxal phosphate (1 wt %), and 10 g of

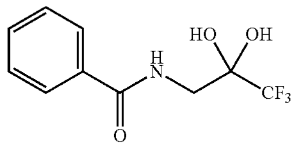 [SMILES: O=C(NCC(O)(O)C(F)(F)F)c1ccccc1]

are added, and stirred uniformly, then 10 ml of transaminase enzyme solution (0.5 wt, 0.5 g/ml), and adjust the pH to 8.5~9.0. The temperature is raised to 10 °C and it is stirred and reacted overnight. After the reaction is completed, the system is adjusted to pH=1, as to denature a protein. After being filtered, filtrate is extracted with 50 mL of dichloromethane. Aqueous phase is adjusted to pH=13, and extracted for three times with 50 ml of dichloromethane. Organic phases are combined and dried with an anhydrous magnesium sulfate, then the organic phase is concentrated until there is no fraction under conditions of T<35 °C and P≤−0.06 Mpa. A target product

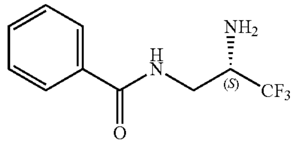

is obtained.

It is detected by HPLC, purity: 98%, ee value: 100%, yield: 90%.

Embodiment 5

50 mL of 100 mmol/L phosphate buffer (5 vol) and 20 mL of 5 mol/L isopropylamine hydrochloride solution (2 vol, 3 eq) are added to a 250 mL four-neck flask at the room temperature, and it is adjusted that pH=7.5-8.0. Then 0.1 g of pyridoxal phosphate (lwt %),

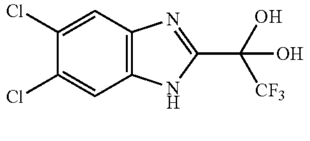 [SMILES: OC(O)(c1nc2cc(Cl)c(Cl)cc2[nH]1)C(F)(F)F]

and 10 g of H are added, and stirred uniformly, then 10 ml of transaminase enzyme solution (0.5 wt, 0.5 g/ml), and adjust the pH to 7.5-8.0. The temperature is raised to 32 °C and it is stirred and reacted overnight. After the reaction is completed, the system is adjusted to pH=1, as to denature a protein. After being filtered, filtrate is extracted with 50 mL of dichloromethane. Aqueous phase is adjusted to pH=13, and extracted for three times with 50 ml of ethyl acetate. Organic phases are combined and dried with an anhydrous magnesium sulfate, then the organic phase is concentrated until there is no fraction under conditions of T<45 °C and P≤−0.08 Mpa. A target product

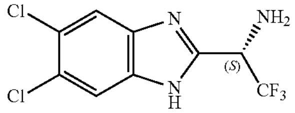

is obtained.

It is detected by HPLC, purity: 98%, ee value: 100%, yield: 87%.

Embodiment 6

50 mL of 100 mmol/L phosphate buffer (5 vol) and 23 mL of 5 mol/L isopropylamine hydrochloride solution (2.3 vol, 3 eq) are added to a 250 mL four-neck flask at the room temperature, and it is adjusted that pH=7.0~7.5. Then 0.1 g of pyridoxal phosphate (1 wt %), and 10 g of

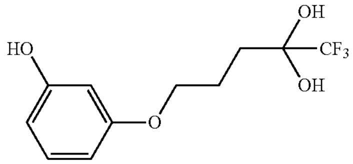 [SMILES: Oc1cccc(OCCCC(O)(O)C(F)(F)F)c1]

are added, and stirred uniformly, then 10 ml of transaminase enzyme solution (0.5 wt, 0.5 g/ml), and adjust the pH to pH=7.0~7.5. The temperature is raised to 28 °C and it is stirred and reacted overnight. After the reaction is completed, the system is adjusted to pH=1, as to denature a protein. After being filtered, filtrate is extracted with 50 mL of dichloromethane. Aqueous phase is adjusted to pH=12, and extracted for three times with 50 ml of dichloromethane. Organic phases are combined and dried with an anhydrous magnesium sulfate, then the organic phase is concentrated until there is no fraction under conditions of T<35 °C and P≤−0.06 Mpa. A target product

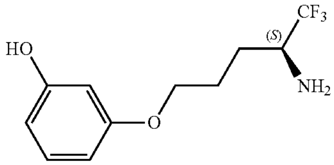

is obtained.

It is detected by HPLC, purity: 98%, ee value: 100%, yield: 80%.

Embodiment 7

200 mL of 100 mmol/L phosphate buffer (10 vol) and 60 mL of 5 mol/L isopropylamine hydrochloride solution (3 vol, 3 eq) are added to a 500 mL four-neck flask at the room temperature, and it is adjusted that pH=7.5~8.0. Then 0.2 g of pyridoxal phosphate (1 wt %), and 20 g of

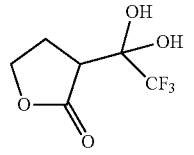 [SMILES: O=C1OCCC1C(O)(O)C(F)(F)F]

are added, and stirred uniformly, then 20 ml of transaminase enzyme solution (0.5 wt, 0.5 g/ml), and adjust the pH to 7.5~8.0. The temperature is raised to 35 °C and it is stirred and reacted overnight. After the reaction is completed, the system is adjusted to pH=1, as to denature a protein. After being filtered, filtrate is extracted with 100 mL of dichloromethane. Aqueous phase is adjusted to pH=12, and extracted for three times with 100 ml of dichloromethane. Organic phases are combined and dried with an anhydrous magnesium sulfate, then the organic phase is concentrated until there is no fraction under conditions of T<35 °C and P≤−0.06 Mpa. A target product

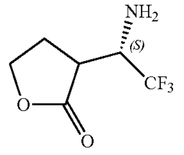

is obtained.

It is detected by HPLC, purity: 94%, ee value: 100%, yield: 82%.

Embodiment 8

80 mL of 100 mmol/L phosphate buffer (8 vol) and 23 mL of 5 mol/L isopropylamine hydrochloride solution (2.3 vol, 3 eq) are added to a 250 mL four-neck flask at the room temperature, and it is adjusted that pH=7.0~7.5. Then 0.1 g of pyridoxal phosphate (1 wt %), and 10 g of

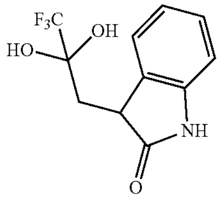 [SMILES: O=C1Nc2ccccc2C1CC(O)(O)C(F)(F)F]

are added, and stirred uniformly, then 20 ml of transaminase enzyme solution (1.0 wt, 0.5 g/ml), and adjust the pH to 7.0~7.5. The temperature is raised to 35 °C and it is stirred and reacted overnight. After the reaction is completed, the system is adjusted to pH=1, as to denature a protein. After being filtered, filtrate is extracted with 50 mL of dichloromethane. Aqueous phase is adjusted to pH=12, and extracted for three times with 50 ml of dichloromethane. Organic phases are combined and dried with an anhydrous magnesium sulfate, then the organic phase is concentrated until there is no fraction under conditions of T<35 °C and P≤−0.06 Mpa. A target product

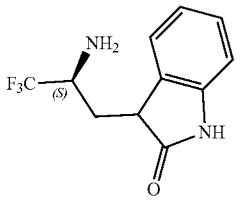

is obtained.

It is detected by HPLC, purity: 97%, ee value: 100%, yield: 86%.

Embodiment 9

50 mL of 100 mmol/L phosphate buffer (10 vol) and 16 mL of 5 mol/L isopropylamine hydrochloride solution (3.2 vol, 3 eq) are added to a 250 mL four-neck flask at the room temperature, and it is adjusted that pH=7.5~8.0. Then 0.05 g of pyridoxal phosphate (1 wt %), and 5 g of

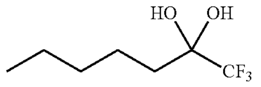

are added, and stirred uniformly, then 10 ml of transaminase enzyme solution (1.0 wt, 0.5 g/ml), and adjust the pH to. The temperature is raised to 20 °C and it is stirred and reacted overnight. After the reaction is completed, the system is adjusted to pH=1, as to denature a protein. After being filtered, filtrate is extracted with 30 mL of dichloromethane. Aqueous phase is adjusted to pH=12, and extracted for three times with 30 ml of dichloromethane. Organic phases are combined and dried with an anhydrous magnesium sulfate, then the organic phase is concentrated until there is no fraction under conditions of T<35 °C and P≤−0.06 Mpa. A target product

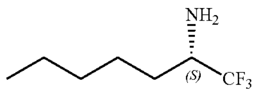

is obtained.

It is detected by a gas chromatography (GC), purity: 95%, ee value: 100%, yield: 78%.

Embodiment 10

50 mL of 100 mmol/L phosphate buffer (10 vol) and 18 mL of 5 mol/L isopropylamine hydrochloride solution (3.6 vol, 3 eq) are added to a 250 mL four-neck flask at the room temperature, and it is adjusted that pH=7.5~8.0. Then 0.05 g of pyridoxal phosphate (1 wt %), and 5 g of

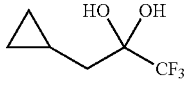

are added, and stirred uniformly, then 10 ml of transaminase enzyme solution (1.0 wt, 0.5 g/ml), and adjust the pH to. The temperature is raised to 25 °C and it is stirred and reacted overnight. After the reaction is completed, the system is adjusted to pH=1, as to denature a protein. After being filtered, filtrate is extracted with 40 mL of dichloromethane. Aqueous phase is adjusted to pH=12, and extracted for three times with 40 ml of dichloromethane. Organic phases are combined and dried with an anhydrous magnesium sulfate, then the organic phase is concentrated until there is no fraction under conditions of T<35 °C and P≤−0.06 Mpa. A target product

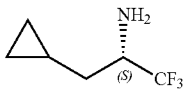

is obtained.

It is detected by GC, purity: 94%, ee value: 100%, yield: 76%.

Embodiment 11

50 mL of 100 mmol/L phosphate buffer (10 vol) and 14 mL of 5 mol/L isopropylamine hydrochloride solution (2.8 vol, 3 eq) are added to a 250 mL four-neck flask at the room temperature, and it is adjusted that pH=7.5~8.0. Then 0.05 g of pyridoxal phosphate (1 wt %), and 5 g of

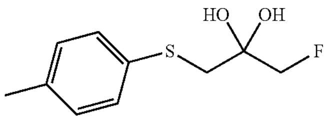

are added, and stirred uniformly, then 10 ml of transaminase enzyme solution (1.0 wt, 0.5 g/ml), and adjust the pH to. The temperature is raised to 25 °C and it is stirred and reacted overnight. After the reaction is completed, the system is adjusted to pH=1, as to denature a protein. After being filtered, filtrate is extracted with 40 mL of dichloromethane. Aqueous phase is adjusted to pH=12, and extracted for three times with 40 ml of dichloromethane. Organic phases are combined and dried with an anhydrous magnesium sulfate, then the organic phase is concentrated until there is no fraction under conditions of T<35 °C and P≤−0.06 Mpa. A target product

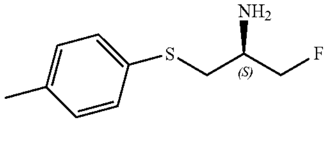

is obtained.

It is detected by HPLC, purity: 92%, ee value: 100%, yield: 79%.

Embodiment 12

60 mL of 100 mmol/L phosphate buffer (12 vol) and 13 mL of 5 mol/L isopropylamine hydrochloride solution (2.6 vol, 3 eq) are added to a 250 mL four-neck flask at the room temperature, and it is adjusted that pH=7.5~8.0. Then 0.05 g of pyridoxal phosphate (1 wt %), and 5 g of

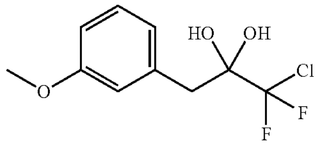 [SMILES: COc1cccc(CC(O)(O)C(F)(F)Cl)c1]

are added, and stirred uniformly, then 10 ml of transaminase enzyme solution (1.0 wt, 0.5 g/ml), and adjust the pH to. The temperature is raised to 35 °C and it is stirred and reacted overnight. After the reaction is completed, the system is adjusted to pH=1, as to denature a protein. After being filtered, filtrate is extracted with 40 mL of dichloromethane. Aqueous phase is adjusted to pH=12, and extracted for three times with 40 ml of dichloromethane. Organic phases are combined and dried with an anhydrous magnesium sulfate, then the organic phase is concentrated until there is no fraction under conditions of T<35 °C and P≤−0.06 Mpa. A target product

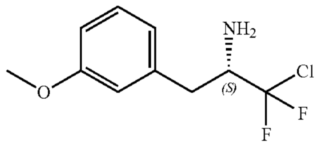

is obtained.

It is detected by HPLC, purity: 95%, ee value: 100%, yield: 84%.

Embodiment 13

Embodiment 1 is taken as an example, the enzyme amount of the reaction is optimized and a specific operation is as follows: 1 mL of 100 mmol/L phosphate buffer (5 vol), and 0.64 ml of 5 mol/L isopropylamine hydrochloride solution (3.2 vol, 3 eq) are added to a 10 mL vial at a room temperature, it is adjusted that pH=7.5~8.0. Then 0.002 g of pyridoxal phosphate (1 wt %), and 0.2 g of

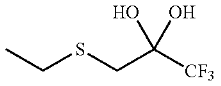

are added, and mixed uniformly, then 0.04 ml, 0.08 ml, 0.12 ml, 0.16 ml, 0.2 ml, 0.24 ml, 0.28 ml, 0.32 ml, 0.36 ml, 0.4 ml, 0.44 ml, 0.48 ml, 0.52 ml, 0.56 ml, and 0.6 ml (the concentration of the enzyme solution is 0.5 g/ml, the corresponding mass ratios are 0.1 wt, 0.2 wt, 0.3 wt, 0.4 wt, 0.5 wt, 0.6 wt, 0.7 wt, 0.8 wt, 0.9 wt, 1.0 wt, 1.1 wt, 1.2 wt, 1.3 wt, 1.4 wt, and 1.5 wt) of transaminase enzyme solution are respectively added, and adjust the pH to 7.5~8.0. The rotation speed of a shaker is 170 rpm, and the temperature is raised to 29 °C and it is reacted overnight.

Conversion rate results are shown in FIG. 1, and it is proved that the conversion rate of 0.5~1.0 wt substrate is greater than 99%, and there is no significant effect while the enzyme amount continues to increase.

Embodiment 14

Embodiment 1 is taken as an example, the substrate concentration is optimized and a specific operation is as follows: 0.3 mL, 0.38 mL, 0.50 mL, 0.62 mL, 0.78 mL, 0.96 ml, 1.16 ml, 1.46 ml, 1.82 ml, 2.28 ml, 2.96 ml, 3.96 ml, 5.56 ml, and 8.96 ml of 100 mmol/L phosphate buffer (1.5 vol, 1.9 vol, 2.5 vol, 3.1 vol, 3.9 vol, 4.8 vol, 5.8 vol, 7.3 vol, 9.1 vol, 11.4 vol, 14.8 vol, 19.8 vol, 27.8 vol, and 44.8 vol respectively), and 0.64 ml of 5 mol/L isopropylamine hydrochloride solution (3.2 vol, 3 eq) are respectively added to a 10-50 mL vial (an appropriate shake flask is selected according to the reaction volume) at the room temperature, it is adjusted that pH=7.5~8.0. Then 0.002 g of pyridoxal phosphate (1 wt %), and 0.2 g of

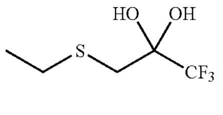

are added, and mixed uniformly, then 0.2 ml of transaminase enzyme solution (0.5 wt, the enzyme solution concentration is 0.5 g/ml), and adjust the pH to 7.5~8.0. The rotation speed of a shaker is 170 rpm, and the temperature is raised to 29 °C and it is reacted overnight.

Figure 2:
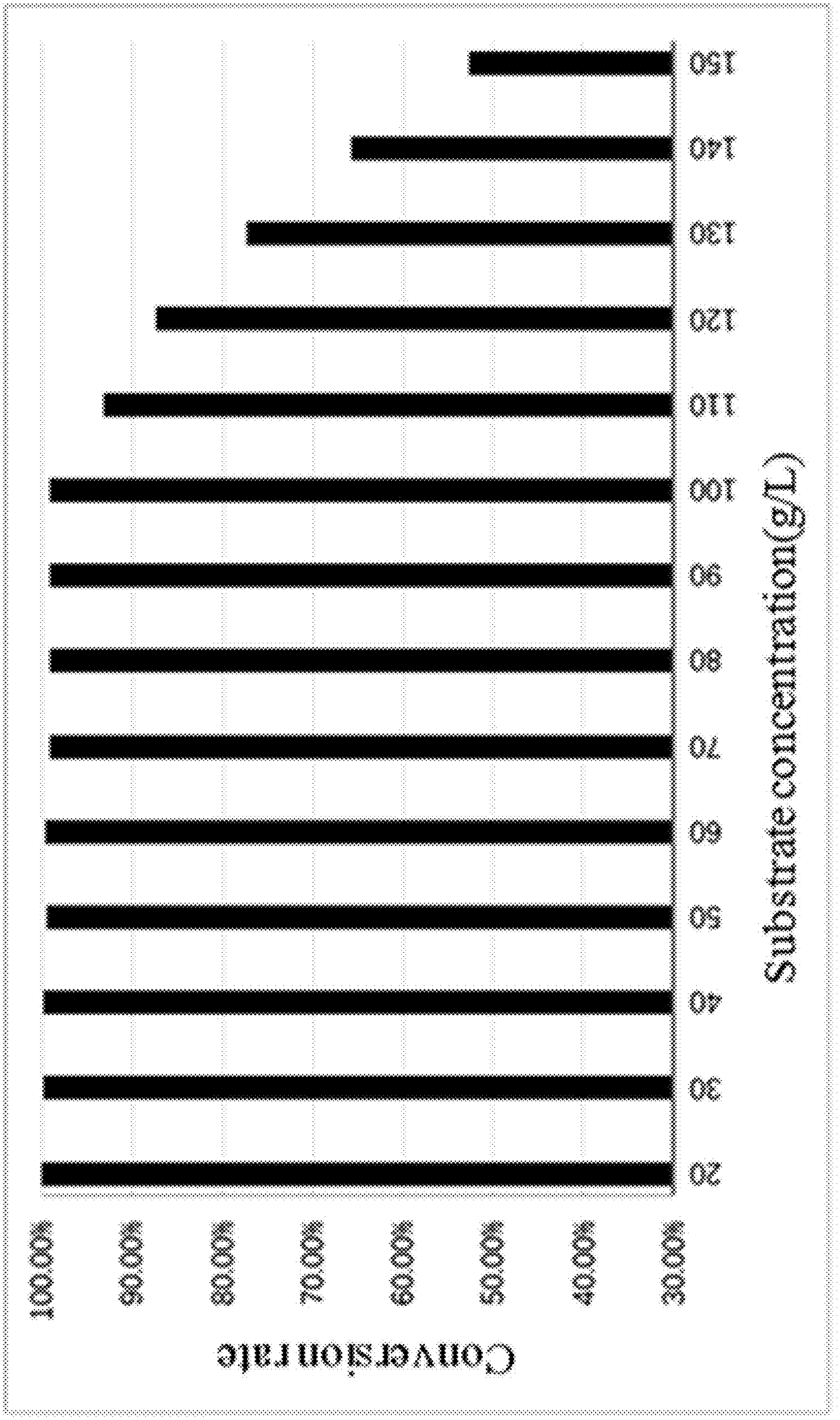
FIG. 2 shows effects of the same enzyme amount on the conversion rate of the substrates with different concentrations in Embodiment 14 of the present invention.

Conversion rate results are shown in FIG. 2, and it is proved that the substrate conversion rate is greater than 99% at the concentration of 60~100 g/L. While the substrate concentration continues to decrease, the reaction volume may be increased, and the amount of three wastes is increased. There is no significant effect.

Embodiment 15

Embodiment 1 is taken as an example, the amino donor is optimized and a specific operation is as follows: 1 ml of 100 mmol/L phosphate buffer (5 vol) is added to a 10-50 mL vial (an appropriate shake flask is selected according to the reaction volume) at the room temperature, and systems of 3 eq amino donors (the amino donors are isopropylamine, isopropylamine hydrochloride, alanine, aniline, and n-butylamine respectively) are used respectively, and it is adjusted that pH=7.5~8.0. Then 0.002 g of pyridoxal phosphate (1 wt %), and 0.2 g of

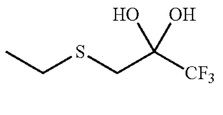

are added, and mixed uniformly, then 0.2 ml of transaminase enzyme solution (0.5 wt, the enzyme solution concentration is 0.5 g/ml), and adjust the pH to 7.5~8.0. The rotation speed of a shaker is 170 rpm, and the temperature is raised to 29 °C and it is reacted overnight.

Figure 3:
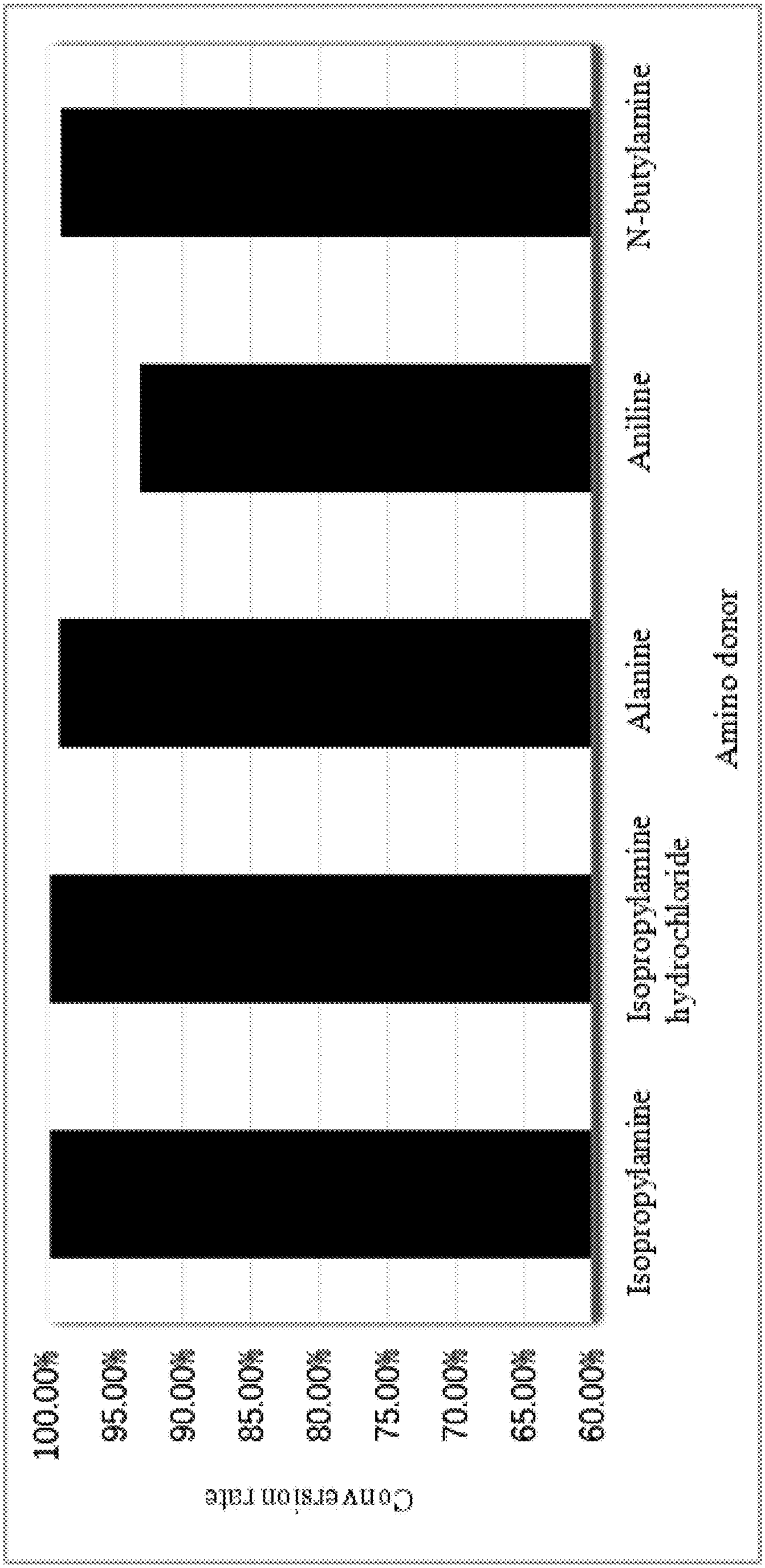
FIG. 3 shows effects of different amino donors on the conversion rate of the substrate in the same reaction in Embodiment 15 of the present invention.

Conversion rate results are shown in FIG. 3, and it is proved that the isopropylamine, isopropylamine hydrochloride, alanine, and n-butylamine are used as the amino donors, and the substrate conversion rate is greater than 99%. While the aniline is used as the amino donor, the conversion rate is 93% under this reaction condition.

Embodiment 16

The substrate of Embodiment 1 is taken as an example, the transaminase derived from *Mycobacterium goodii* (GenBank: AKS36000.1) is numbered as TA1, the transaminase derived from *Fonsecaea pedrosoi* CBS 271.37 (NCBI Reference Sequence: XP_013286281.1) is numbered as TA2, the transaminase derived from *Klebsiella pneumoniae* subsp. *pneumoniae* Ecl8 (GenBank: CCN29541.1) is numbered as TA3, the transaminase derived from *Chromobacterium violaceum* DSM30191 (CVTA) (NCBI Reference Sequence: WP_011135573.1) is numbered as TA4, the transaminase derived from *Paracoccus denitrificans* (NCBI Reference Sequence: WP_011746975.1) is numbered as TA5, the transaminase derived from *Penicillium brasilianum* (GenBank: CEJ55334.1) is numbered as TA6, the transaminase derived from *Enterobacter* sp.TL3 (NCBI Reference Sequence: WP_014885677.1) is numbered as TA7, the transaminase derived from *Aspergillus terreus* NIH2624 (NCBI Reference Sequence: XP_001209325.1) is numbered as TA8, the transaminase derived from *Exophiala spinifera* (NCBI Reference Sequence: XP_016233821.1) is numbered as TA9, the transaminase derived from *Deinococcus geothermalis* (strain DSM 11300) (NCBI Reference Sequence: WP_011530545.1) is numbered as TA10, the transaminase derived from *Geomyces destructans* 20631-21 (GdTA) in *E. coli* (GenBank: ELR05573.1) is numbered as TA11, the transaminase derived from *Pseudomonas putida* KT2440 (NCBI Reference Sequence: WP_010954554.1) is numbered as TA12, the transaminase derived from *Lysinibacillus sphaericus* (NCBI Reference Sequence: WP_024363741.1) is numbered as TA13, the transaminase derived from *Bacillus megaterium* DSM 319 (NCBI Reference Sequence: WP_013082219.1) is numbered as TA14, the transaminase derived from *Trichoderma harzianum* (GenBank: KKP07030.1) is numbered as TA15, the transaminase derived from *Aspergillus fumigatus* R-ATAs (AspFum) (NCBI Reference Sequence: XP_748821.1) is numbered as TA16, the transaminase derived from *Geobacillus thermodenitrificans* subsp. *thermodenitrificans* DSM 465 (NCBI Reference Sequence: WP_008879436.1) is numbered as TA17, the transaminase derived from *Cladophialophora bantiana* CBS 173.52 (NCBI Reference Sequence: XP_016617948.1) is numbered as TA18, the transaminase derived from *Bacillus megaterium* (NCBI Reference Sequence: WP_016763026.1) is numbered as TA19, the transaminase derived from *Burkholderia thailandensis* MSMB121 (BtS-TA) (GenBank: AGK49399.1) is numbered as TA20, the transaminase derived from *Klebsiella pneumoniae* subsp. *pneumoniae* MGH 78578 (NCBI Reference Sequence: WP_002920226.1) is numbered as TA21, the transaminase derived from *Geobacillus toebii* (NCBI Reference Sequence: WP_062753894.1) is numbered as TA22, the transaminase derived from *Talaromyces cellulolyticus* (GenBank: GAM37533.1) is numbered as TA23, mutants TA4-V1 (a corresponding sequence is SEQ ID NO: 1), TA4-V2 (a corresponding sequence is SEQ ID NO: 2), TA4-V3 (a corresponding sequence is SEQ ID NO: 3), and TA4-V4 (a corresponding sequence is SEQ ID NO: 4) obtained by evolution of the transaminase derived from *Chromobacterium violaceum* DSM30191 (CVTA) (NCBI Reference Sequence: WP_011135573.1) perform a 10 mg-level screening reaction, and an operation is as follows.

100 mmol/L phosphate buffer and 5 mol/L isopropylamine hydrochloride solution are prepared into 50 ml of solution according to a volume ratio of 5:2, and then 0.005 g of pyridoxal phosphate is added, and it is stirred and mixed uniformly. 0.3 ml of the above solution is taken and added to a 96-well plate respectively, and 10 mg of

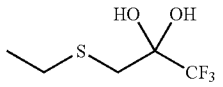

is added, and then 0.2 ml of the above enzyme solution (10 wt, the concentration of the enzyme solution is 0.5 g/ml) is added respectively, the rotation speed of a shaker is 170 rpm, the temperature is raised to 30 °C and it is reacted overnight.

Figure 4:
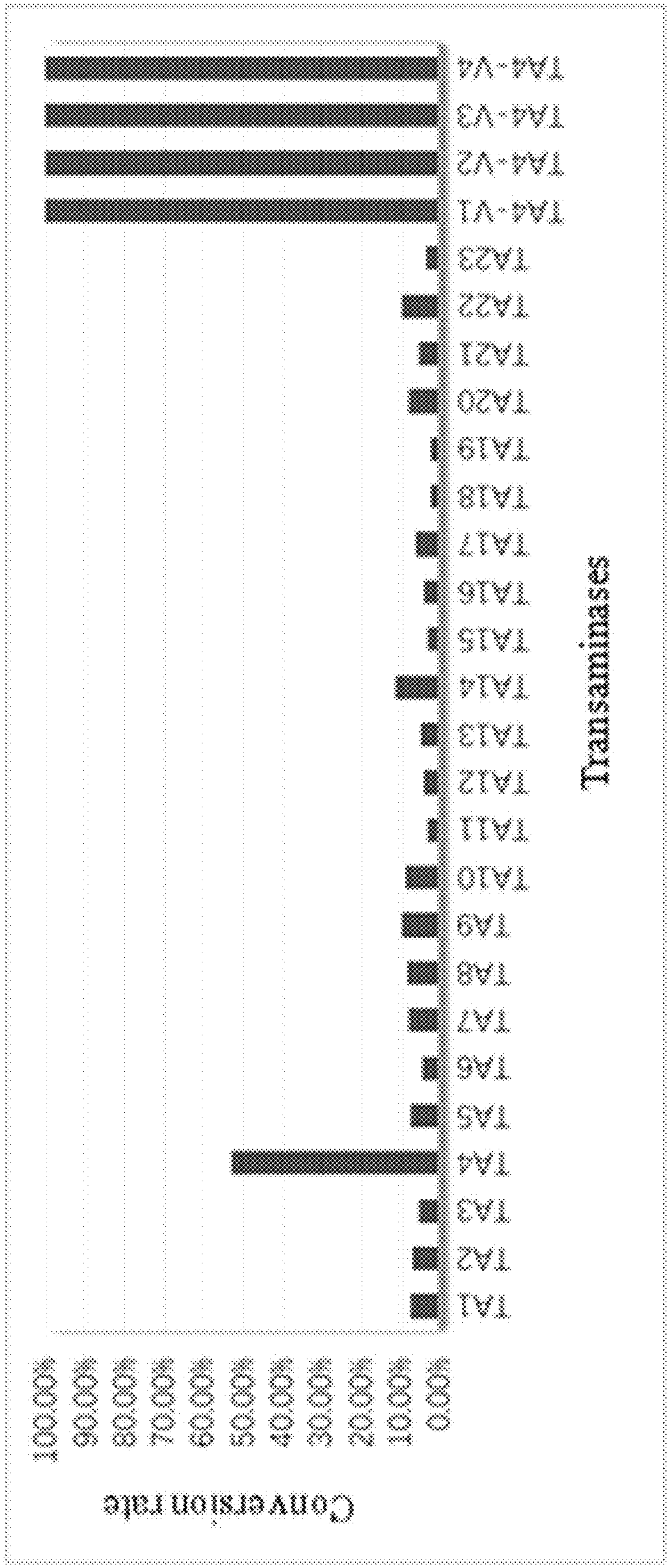
FIG. 4 shows that transaminases from different sources in Embodiment 16 of the present invention all have conversion activities for the same substrate.

Screening results are shown in FIG. 4: it is proved that all the enzymes from all sources have the catalytic activity on the substrate, the transaminase derived from *Chromobacterium violaceum* DSM30191 (CVTA) is the best, and the transaminase derived from *Chromobacterium violaceum* DSM30191 (CVTA) is mutated, and four mutants obtained have the better conversion rates, and the conversion rates are all greater than 99%.

From the above descriptions, it may be seen that the above embodiments of the present invention achieve the following technical effects.

1. It is not found yet that there is a patent for converting the similar compound with an invertase.
2. The biotransformation reaction using the transaminase may directly obtain the desired target compound by the one-step reaction, and the substrate types are widely applicable.
3. The use of the transaminase for this biotransformation reaction has the high selectivity, and the ee value of the product is greatly improved.
4. The self-extracted transaminase is used, the substrate concentration may reach 100 g/L, the production efficiency is greatly improved, and the generation of the organic solvents and three wastes is reduced.
5. The transaminase is high in catalytic efficiency; and the reaction which uses the transaminase is small in reaction volume, short in synthesis route, and has high product yield; and the production cost is greatly reduced.

The above are only preferred embodiments of the present invention, and are not intended to limit the present invention. For those skilled in the art, the present invention may have various modifications and changes. Any modifications, equivalent replacements, improvements and the like made within the spirit and principle of the present invention shall be included within a scope of protection of the present invention.

What is claimed is:

1. A method for synthesizing a fluorine-containing chiral amine compound, wherein the method comprises:

reacting an amino donor with a fluorine-containing dihydroxy ketal compound under a catalysis of a transaminase to generate the fluorine-containing chiral amine compound;

wherein the transaminase has the amino acid sequence of SEQ ID NO:4; of;

the fluorine-containing dihydroxy ketal compound is selected from any one of the group consisting of:

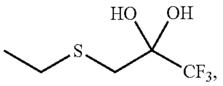,
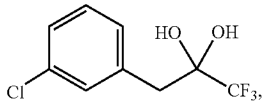,
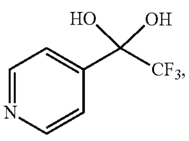,
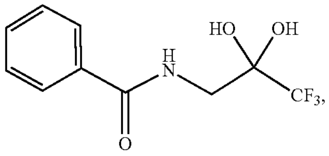,
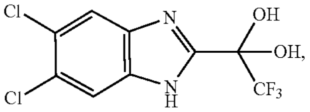,
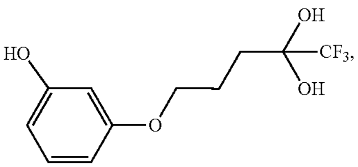,

-continued

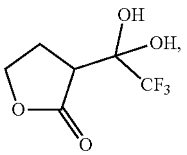,
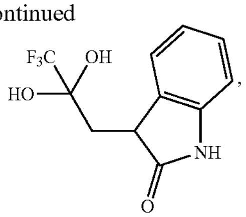,
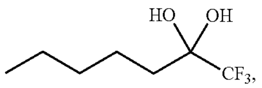,
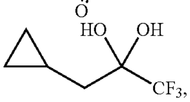,
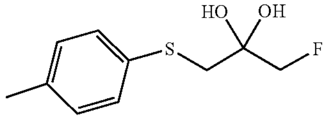

and

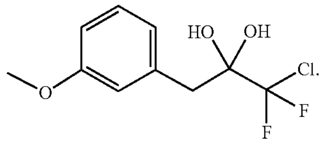.

2. The method according to claim 1, wherein the method comprises:

(i) mixing a phosphate buffer with the amino donor to obtain a first mixed solution;

(ii) adding the fluorine-containing dihydroxy ketal compound to the first mixed solution to obtain a second mixed solution;

(iii) adding the transaminase to the second mixed solution to obtain a reaction mixture; and (iv) isolating the fluorine-containing chiral amine compound from the reaction mixture.

3. The method according to claim 2, wherein before adding the fluorine-containing dihydroxy ketal compound to the first mixed solution, the method further comprises: adjusting a pH value of the first mixed solution to 7.0-9.0.

4. The method according to claim 2, wherein the step (iii) comprises:

(iii-1) adding the transaminase to the second mixed solution, and (iii-2) adjusting a pH of the second mixed solution after addition of the transaminase to 7.0-9.0, thereby obtaining the reaction mixture.

5. The method according to claim 2, wherein isolating the fluorine-containing chiral amine compound from the reaction mixture comprises:

adjusting the acidity of the reaction mixture to denature the transaminase to obtain a denatured transaminase;

filtering and removing the denatured transaminase to obtain a filtrate;

extracting the filtrate to obtain the fluorine-containing chiral amine compound.

6. The method according to claim 5, wherein adjusting the acidity of the reaction mixture comprises adjusting a pH value of the reaction mixture to 1-2.

7. The method according to claim 5, wherein the filtering is carried out with dichloromethane.

8. The method according to claim 5, wherein the extracting is carried out with dichloromethane.

9. The method according to claim 5, wherein the extracting the filtrate carried out 2-5 times, and after the extracting the filtrate, a step of drying organic phases resulting from the extracting the filtrate is further included.

10. The method according to claim 5, wherein combining organic phases obtained from the extracting the filtrate to obtain an extract;

drying the extract to obtain a dried organic phase of product;

concentrating the dried organic phase of product to no fraction under a temperature less than 35 °C and a pressure no more than −0.06 Mpa to obtain the fluorine-containing chiral amine compound.

11. The method according to claim 1, wherein a mass ratio of the transaminase to the fluorine-containing dihydroxy ketal compound is 0.4:1 to 1.0:1.

12. The method according to claim 1, wherein a concentration of the fluorine-containing dihydroxy ketal compound is 60 g/L to 100 g/L.

13. The method according to claim 1, wherein the amino donor is selected from any one of the group consisting of isopropylamine, isopropylamine hydrochloride, alanine, aniline and n-butylamine.

* * * * *

SEQUENCE LISTING

```
<160> NUMBER OF SEQ ID NOS: 27

<210> SEQ ID NO 1
<211> LENGTH: 459
<212> TYPE: PRT
<213> ORGANISM: Chromobacterium violaceum DSM30191
<220> FEATURE:
<221> NAME/KEY: VARIANT
<222> LOCATION: (1)..(459)
<223> OTHER INFORMATION: TA4-V1

<400> SEQUENCE: 1

Met Gln Lys Gln Arg Thr Cys Ser Gln Trp Arg Glu Leu Asp Ala Ala
1               5                   10                  15

His His Leu His Pro Phe Thr Asp Thr Ala Ser Leu Asn Gln Ala Gly
            20                  25                  30

Ala Arg Val Met Thr Arg Gly Glu Gly Val Tyr Leu Trp Asp Cys Glu
        35                  40                  45

Gly Asn Lys Ile Ile Asp Gly Met Ala Gly Leu Trp Cys Val Asn Val
    50                  55                  60

Gly Tyr Gly Arg Lys Asp Phe Ala Glu Ala Ala Arg Arg Gln Met Glu
65                  70                  75                  80

Glu Leu Pro Phe Tyr Asn Thr Phe Tyr Lys Thr Thr His Pro Ala Val
                85                  90                  95

Val Glu Leu Ser Ser Leu Leu Ala Glu Val Thr Pro Ala Gly Phe Asp
            100                 105                 110

Arg Val Phe Tyr Thr Asn Ser Gly Ser Glu Ser Val Asp Thr Met Ile
        115                 120                 125

Arg Met Val Arg Arg Tyr Trp Asp Val Gln Gly Lys Pro Glu Lys Lys
    130                 135                 140

Thr Leu Ile Gly Arg Trp Trp Gly Tyr His Gly Ser Thr Ile Gly Gly
145                 150                 155                 160

Ala Ser Leu Gly Gly Phe Lys Tyr Met His Glu Gln Gly Asp Leu Pro
                165                 170                 175

Ile Pro Gly Met Ala His Ile Glu Gln Pro Trp Trp Tyr Lys His Gly
            180                 185                 190
```

Lys Asp Met Thr Pro Asp Glu Phe Gly Val Val Ala Ala Arg Trp Leu
195 200 205

Glu Glu Lys Ile Leu Glu Ile Gly Ala Asp Lys Val Ala Ala Phe Val
210 215 220

Gly Glu Pro Ile Gln Gly Ala Gly Gly Val Ile Val Pro Pro Ala Thr
225 230 235 240

Tyr Trp Pro Glu Ile Glu Arg Ile Cys Arg Lys Tyr Asp Val Leu Leu
245 250 255

Val Ala Asp Glu Val Ile Cys Gly Phe Gly Arg Thr Gly Glu Trp Phe
260 265 270

Gly His Gln His Phe Gly Phe Gln Pro Asp Leu Phe Thr Ala Ala Lys
275 280 285

Gly Leu Ser Ser Gly Tyr Leu Pro Ile Gly Ala Val Phe Val Gly Lys
290 295 300

Arg Val Ala Glu Gly Leu Ile Ala Gly Gly Asp Phe Asn His Gly Phe
305 310 315 320

Thr Tyr Ser Gly His Pro Val Cys Ala Ala Val Ala His Ala Asn Val
325 330 335

Ala Ala Leu Arg Asp Glu Gly Ile Val Gln Arg Val Lys Asp Asp Ile
340 345 350

Gly Pro Tyr Met Gln Lys Arg Trp Arg Glu Thr Phe Ser Arg Phe Glu
355 360 365

His Val Asp Asp Val Arg Gly Val Gly Met Leu Leu Ala Phe Thr Leu
370 375 380

Val Lys Asn Lys Ala Lys Arg Glu Leu Phe Pro Asp Phe Gly Glu Ile
385 390 395 400

Gly Thr Leu Cys Arg Asp Ile Phe Phe Arg Asn Asn Leu Ile Met Asp
405 410 415

Ser Cys Gly Asp His Ile Val Cys Ala Pro Pro Leu Val Met Thr Arg
420 425 430

Ala Glu Val Asp Glu Met Leu Ala Val Ala Glu Arg Cys Leu Glu Glu
435 440 445

Phe Glu Gln Thr Leu Lys Ala Arg Gly Leu Ala
450 455

<210> SEQ ID NO 2
<211> LENGTH: 459
<212> TYPE: PRT
<213> ORGANISM: Chromobacterium violaceum DSM30191
<220> FEATURE:
<221> NAME/KEY: VARIANT
<222> LOCATION: (1)..(459)
<223> OTHER INFORMATION: TA4-V2

<400> SEQUENCE: 2

Met Gln Lys Gln Arg Thr Cys Ser Gln Trp Arg Glu Leu Asp Ala Ala
1 5 10 15

His His Leu His Pro Phe Thr Asp Thr Ala Ser Leu Asn Gln Ala Gly
20 25 30

Ala Arg Val Met Thr Arg Gly Glu Gly Val Tyr Leu Trp Asp Cys Glu
35 40 45

Gly Asn Lys Ile Ile Asp Gly Met Ala Gly Leu Trp Cys Val Asn Val
50 55 60

Gly Tyr Gly Arg Lys Asp Phe Ala Glu Ala Ala Arg Arg Gln Met Glu
65 70 75 80

-continued

```
Glu Leu Pro Phe Tyr Asn Thr Phe Tyr Lys Thr Thr His Pro Ala Val
                85                  90                  95

Val Glu Leu Ser Ser Leu Leu Ala Glu Val Thr Pro Ala Gly Phe Asp
            100                 105                 110

Arg Val Phe Tyr Thr Asn Ser Gly Ser Glu Ser Val Asp Thr Met Ile
        115                 120                 125

Arg Met Val Arg Arg Tyr Trp Asp Val Gln Gly Lys Pro Glu Lys Lys
    130                 135                 140

Thr Leu Ile Gly Arg Trp Trp Gly Tyr His Gly Ser Thr Ile Gly Gly
145                 150                 155                 160

Ala Ser Leu Gly Gly Phe Lys Tyr Met His Glu Gln Gly Asp Leu Pro
                165                 170                 175

Ile Pro Gly Met Ala His Ile Glu Gln Pro Trp Trp Tyr Lys His Gly
            180                 185                 190

Lys Asp Met Thr Pro Asp Glu Phe Gly Val Val Ala Ala Arg Trp Leu
        195                 200                 205

Glu Glu Lys Ile Leu Glu Ile Gly Ala Asp Lys Val Ala Ala Phe Val
    210                 215                 220

Gly Glu Pro Ile Gln Gly Ala Gly Gly Val Ile Val Pro Pro Ala Thr
225                 230                 235                 240

Tyr Trp Pro Glu Ile Glu Arg Ile Cys Arg Lys Tyr Asp Val Leu Leu
                245                 250                 255

Val Ala Asp Glu Val Ile Cys Gly Phe Gly Arg Thr Gly Glu Trp Phe
            260                 265                 270

Gly His Gln His Phe Gly Phe Gln Pro Asp Leu Phe Thr Ala Ala Lys
        275                 280                 285

Gly Leu Ser Ser Gly Tyr Leu Pro Ile Gly Ala Val Phe Val Gly Lys
    290                 295                 300

Arg Val Ala Glu Gly Leu Ile Ala Gly Gly Asp Phe Asn His Gly Phe
305                 310                 315                 320

Thr Tyr Ser Gly His Pro Val Cys Ala Ala Val Ala His Ala Asn Val
                325                 330                 335

Ala Ala Leu Arg Asp Glu Gly Ile Val Gln Arg Val Lys Asp Asp Ile
            340                 345                 350

Gly Pro Tyr Met Gln Lys Arg Trp Arg Glu Thr Phe Ser Arg Phe Glu
        355                 360                 365

His Val Asp Asp Val Arg Gly Val Gly Met Leu Leu Ala Phe Thr Leu
    370                 375                 380

Val Lys Asn Lys Ala Lys Arg Glu Leu Phe Pro Asp Phe Gly Glu Ile
385                 390                 395                 400

Gly Thr Leu Cys Arg Asp Ile Phe Phe Arg Asn Asn Leu Ile Met Asp
                405                 410                 415

Ser Cys Gly Asp His Ile Val Ala Ala Pro Pro Leu Val Met Thr Arg
            420                 425                 430

Ala Glu Val Asp Glu Met Leu Ala Val Ala Glu Arg Cys Leu Glu Glu
        435                 440                 445

Phe Glu Gln Thr Leu Lys Ala Arg Gly Leu Ala
    450                 455
```

<210> SEQ ID NO 3
<211> LENGTH: 459
<212> TYPE: PRT
<213> ORGANISM: Chromobacterium violaceum DSM30191
<220> FEATURE:
<221> NAME/KEY: VARIANT

<222> LOCATION: (1)..(459)
<223> OTHER INFORMATION: TA4-V3

<400> SEQUENCE: 3

```
Met Gln Lys Gln Arg Thr Cys Ser Gln Trp Arg Glu Leu Asp Ala Ala
1               5                   10                  15

His His Leu His Pro Phe Thr Asp Thr Ala Ser Leu Asn Gln Ala Gly
            20                  25                  30

Ala Arg Val Met Thr Arg Gly Glu Gly Val Tyr Leu Trp Asp Cys Glu
        35                  40                  45

Gly Asn Lys Ile Ile Asp Gly Met Ala Gly Leu Trp Cys Val Asn Val
    50                  55                  60

Gly Tyr Gly Arg Lys Asp Phe Ala Glu Ala Ala Arg Arg Gln Met Glu
65                  70                  75                  80

Glu Leu Pro Phe Tyr Asn Thr Phe Tyr Lys Thr Thr His Pro Ala Val
                85                  90                  95

Val Glu Leu Ser Ser Leu Leu Ala Glu Val Thr Pro Ala Gly Phe Asp
            100                 105                 110

Arg Val Phe Tyr Thr Asn Ser Gly Ser Glu Ser Val Asp Thr Met Ile
        115                 120                 125

Arg Met Val Arg Arg Tyr Trp Asp Val Gln Gly Lys Pro Glu Lys Lys
    130                 135                 140

Thr Leu Ile Gly Arg Trp Trp Gly Tyr His Gly Ser Thr Ile Gly Gly
145                 150                 155                 160

Ala Ser Leu Gly Gly Phe Lys Tyr Met His Glu Gln Gly Asp Leu Pro
                165                 170                 175

Ile Pro Gly Met Ala His Ile Glu Gln Pro Trp Trp Tyr Lys His Gly
            180                 185                 190

Lys Asp Met Thr Pro Asp Glu Phe Gly Val Val Ala Ala Arg Trp Leu
        195                 200                 205

Glu Glu Lys Ile Leu Glu Ile Gly Ala Asp Lys Val Ala Ala Phe Val
    210                 215                 220

Gly Glu Pro Ile Gln Gly Ala Gly Gly Val Ile Val Pro Pro Ala Thr
225                 230                 235                 240

Tyr Trp Pro Glu Ile Glu Arg Ile Cys Arg Lys Tyr Asp Val Leu Leu
                245                 250                 255

Val Ala Asp Glu Val Ile Cys Gly Phe Gly Arg Thr Gly Glu Trp Phe
            260                 265                 270

Gly His Gln His Phe Gly Phe Gln Pro Asp Leu Phe Thr Ala Ala Lys
        275                 280                 285

Gly Leu Ser Ser Gly Tyr Leu Pro Ile Gly Ala Val Phe Val Gly Lys
    290                 295                 300

Arg Val Ala Glu Gly Leu Ile Ala Gly Gly Asp Phe Asn His Gly Phe
305                 310                 315                 320

Thr Tyr Ser Gly His Pro Val Cys Ala Ala Val Ala His Ala Asn Val
                325                 330                 335

Ala Ala Leu Arg Asp Glu Gly Ile Val Gln Arg Val Lys Asp Asp Ile
            340                 345                 350

Gly Pro Tyr Met Gln Lys Arg Trp Arg Glu Thr Phe Ser Arg Phe Glu
        355                 360                 365

His Val Asp Asp Val Arg Gly Val Gly Met Leu Leu Ala Phe Thr Leu
    370                 375                 380

Val Lys Asn Lys Ala Lys Arg Glu Leu Phe Pro Asp Phe Gly Glu Ile
385                 390                 395                 400
```

```
Gly Thr Leu Cys Arg Asp Ile Phe Gln Arg Asn Asn Leu Ile Met Asp
                405                 410                 415

Ser Cys Gly Asp His Ile Val Ser Ala Pro Pro Leu Val Met Thr Arg
            420                 425                 430

Ala Glu Val Asp Glu Met Leu Ala Val Ala Glu Arg Cys Leu Glu Glu
        435                 440                 445

Phe Glu Gln Thr Leu Lys Ala Arg Gly Leu Ala
    450                 455


<210> SEQ ID NO 4
<211> LENGTH: 459
<212> TYPE: PRT
<213> ORGANISM: Chromobacterium violaceum DSM30191
<220> FEATURE:
<221> NAME/KEY: VARIANT
<222> LOCATION: (1)..(459)
<223> OTHER INFORMATION: TA4-V4

<400> SEQUENCE: 4

Met Gln Lys Gln Arg Thr Cys Ser Gln Trp Arg Glu Leu Asp Ala Ala
1               5                   10                  15

His His Leu His Pro Phe Thr Asp Thr Ala Ser Leu Asn Gln Ala Gly
            20                  25                  30

Ala Arg Val Met Thr Arg Gly Glu Gly Val Tyr Leu Trp Asp Cys Glu
        35                  40                  45

Gly Asn Lys Ile Ile Asp Gly Met Ala Gly Leu Trp Cys Val Asn Val
    50                  55                  60

Gly Tyr Gly Arg Lys Asp Phe Ala Glu Ala Ala Arg Arg Gln Met Glu
65                  70                  75                  80

Glu Leu Pro Phe Tyr Asn Thr Phe Tyr Lys Thr Thr His Pro Ala Val
                85                  90                  95

Val Glu Leu Ser Ser Leu Leu Ala Glu Val Thr Pro Ala Gly Phe Asp
            100                 105                 110

Arg Val Phe Tyr Thr Asn Ser Gly Ser Glu Ser Val Asp Thr Met Ile
        115                 120                 125

Arg Met Val Arg Arg Tyr Trp Asp Val Gln Gly Lys Pro Glu Lys Lys
    130                 135                 140

Thr Leu Ile Gly Arg Trp Trp Gly Tyr His Gly Ser Thr Ile Gly Gly
145                 150                 155                 160

Ala Ser Leu Gly Gly Phe Lys Tyr Met His Glu Gln Gly Asp Leu Pro
                165                 170                 175

Ile Pro Gly Met Ala His Ile Glu Gln Pro Trp Trp Tyr Lys His Gly
            180                 185                 190

Lys Asp Met Thr Pro Asp Glu Phe Gly Val Val Ala Ala Arg Trp Leu
        195                 200                 205

Glu Glu Lys Ile Leu Glu Ile Gly Ala Asp Lys Val Ala Ala Phe Val
    210                 215                 220

Gly Glu Pro Ile Gln Gly Ala Gly Gly Val Ile Val Pro Pro Ala Thr
225                 230                 235                 240

Tyr Trp Pro Glu Ile Glu Arg Ile Cys Arg Lys Tyr Asp Val Leu Leu
                245                 250                 255

Val Ala Asp Glu Val Ile Cys Gly Phe Gly Arg Thr Gly Glu Trp Phe
            260                 265                 270

Gly His Gln His Phe Gly Phe Gln Pro Asp Leu Phe Thr Ala Ala Lys
        275                 280                 285
```

-continued

```
Gly Leu Ser Ser Gly Tyr Leu Pro Ile Gly Ala Val Phe Val Gly Lys
    290                 295                 300

Arg Val Ala Glu Gly Leu Ile Ala Gly Gly Asp Phe Asn His Gly Phe
305                 310                 315                 320

Thr Tyr Ser Gly His Pro Val Cys Ala Ala Val Ala His Ala Asn Val
                325                 330                 335

Ala Ala Leu Arg Asp Glu Gly Ile Val Gln Arg Val Lys Asp Asp Ile
            340                 345                 350

Gly Pro Tyr Met Gln Lys Arg Trp Arg Glu Thr Phe Ser Arg Phe Glu
        355                 360                 365

His Val Asp Asp Val Arg Gly Val Gly Met Leu Leu Ala Phe Thr Leu
    370                 375                 380

Val Lys Asn Lys Ala Lys Arg Glu Leu Phe Pro Asp Phe Gly Glu Ile
385                 390                 395                 400

Gly Thr Leu Cys Arg Asp Ile Phe His Arg Asn Asn Leu Ile Met Asp
                405                 410                 415

Ser Cys Gly Asp His Ile Val Ser Ala Pro Pro Leu Val Met Thr Arg
            420                 425                 430

Ala Glu Val Asp Glu Met Leu Ala Val Ala Glu Arg Cys Leu Glu Glu
        435                 440                 445

Phe Glu Gln Thr Leu Lys Ala Arg Gly Leu Ala
    450                 455


<210> SEQ ID NO 5
<211> LENGTH: 459
<212> TYPE: PRT
<213> ORGANISM: Chromobacterium violaceum DSM30191

<400> SEQUENCE: 5

Met Gln Lys Gln Arg Thr Thr Ser Gln Trp Arg Glu Leu Asp Ala Ala
1               5                   10                  15

His His Leu His Pro Phe Thr Asp Thr Ala Ser Leu Asn Gln Ala Gly
            20                  25                  30

Ala Arg Val Met Thr Arg Gly Glu Gly Val Tyr Leu Trp Asp Ser Glu
        35                  40                  45

Gly Asn Lys Ile Ile Asp Gly Met Ala Gly Leu Trp Cys Val Asn Val
    50                  55                  60

Gly Tyr Gly Arg Lys Asp Phe Ala Glu Ala Ala Arg Arg Gln Met Glu
65                  70                  75                  80

Glu Leu Pro Phe Tyr Asn Thr Phe Phe Lys Thr Thr His Pro Ala Val
                85                  90                  95

Val Glu Leu Ser Ser Leu Leu Ala Glu Val Thr Pro Ala Gly Phe Asp
            100                 105                 110

Arg Val Phe Tyr Thr Asn Ser Gly Ser Glu Ser Val Asp Thr Met Ile
        115                 120                 125

Arg Met Val Arg Arg Tyr Trp Asp Val Gln Gly Lys Pro Glu Lys Lys
    130                 135                 140

Thr Leu Ile Gly Arg Trp Asn Gly Tyr His Gly Ser Thr Ile Gly Gly
145                 150                 155                 160

Ala Ser Leu Gly Gly Met Lys Tyr Met His Glu Gln Gly Asp Leu Pro
                165                 170                 175

Ile Pro Gly Met Ala His Ile Glu Gln Pro Trp Trp Tyr Lys His Gly
            180                 185                 190

Lys Asp Met Thr Pro Asp Glu Phe Gly Val Val Ala Ala Arg Trp Leu
        195                 200                 205
```

Glu Glu Lys Ile Leu Glu Ile Gly Ala Asp Lys Val Ala Ala Phe Val
    210                 215                 220

Gly Glu Pro Ile Gln Gly Ala Gly Gly Val Ile Val Pro Pro Ala Thr
225                 230                 235                 240

Tyr Trp Pro Glu Ile Glu Arg Ile Cys Arg Lys Tyr Asp Val Leu Leu
                245                 250                 255

Val Ala Asp Glu Val Ile Cys Gly Phe Gly Arg Thr Gly Glu Trp Phe
            260                 265                 270

Gly His Gln His Phe Gly Phe Gln Pro Asp Leu Phe Thr Ala Ala Lys
        275                 280                 285

Gly Leu Ser Ser Gly Tyr Leu Pro Ile Gly Ala Val Phe Val Gly Lys
    290                 295                 300

Arg Val Ala Glu Gly Leu Ile Ala Gly Gly Asp Phe Asn His Gly Phe
305                 310                 315                 320

Thr Tyr Ser Gly His Pro Val Cys Ala Ala Val Ala His Ala Asn Val
                325                 330                 335

Ala Ala Leu Arg Asp Glu Gly Ile Val Gln Arg Val Lys Asp Asp Ile
            340                 345                 350

Gly Pro Tyr Met Gln Lys Arg Trp Arg Glu Thr Phe Ser Arg Phe Glu
        355                 360                 365

His Val Asp Asp Val Arg Gly Val Gly Met Val Gln Ala Phe Thr Leu
    370                 375                 380

Val Lys Asn Lys Ala Lys Arg Glu Leu Phe Pro Asp Phe Gly Glu Ile
385                 390                 395                 400

Gly Thr Leu Cys Arg Asp Ile Phe Phe Arg Asn Asn Leu Ile Met Arg
                405                 410                 415

Ala Cys Gly Asp His Ile Val Ser Ala Pro Pro Leu Val Met Thr Arg
            420                 425                 430

Ala Glu Val Asp Glu Met Leu Ala Val Ala Glu Arg Cys Leu Glu Glu
        435                 440                 445

Phe Glu Gln Thr Leu Lys Ala Arg Gly Leu Ala
    450                 455

<210> SEQ ID NO 6
<211> LENGTH: 342
<212> TYPE: PRT
<213> ORGANISM: Fonsecaea pedrosoi CBS 271.37

<400> SEQUENCE: 6

Met Thr Ser Met Ala Lys Val Phe Gly Ala Tyr Glu Ala Arg Lys Ala
1               5                   10                  15

Leu Leu Glu Lys Ser Thr Asn Pro Leu Ala Gln Gly Val Ala Trp Val
            20                  25                  30

Glu Gly Gln Leu Tyr Pro Ile Asn Glu Ala Arg Ile Pro Leu Met Asp
        35                  40                  45

Gln Gly Phe Leu His Ser Asp Leu Thr Tyr Asp Val Pro Ser Val Trp
    50                  55                  60

Asp Gly Arg Phe Phe Arg Leu Asp Asp His Leu Ser Arg Leu Glu Lys
65                  70                  75                  80

Ser Cys Ala Lys Met Arg Leu Lys Leu Pro Val Pro Arg Asp Glu Val
                85                  90                  95

Lys Arg Ile Leu Cys Asp Met Val Ala Lys Ser Gly Ile Arg Asp Ala
            100                 105                 110

Phe Val Glu Leu Ile Val Thr Arg Gly Leu Lys Gly Val Arg Gly Thr

```
        115                 120                 125

Arg Asn Pro Glu Asp Leu Thr Asn Ser Leu Tyr Leu Phe Ile Thr Pro
    130                 135                 140

Tyr Leu Trp Val Met Glu Pro Glu Met Gln Leu His Gly Ser Gly Ser
145                 150                 155                 160

Ala Ile Ile Ala Arg Thr Val Arg Arg Thr Pro Pro Gly Cys Met Asp
                165                 170                 175

Pro Thr Val Lys Asn Leu Gln Trp Gly Asp Leu Thr Arg Ala Met Leu
            180                 185                 190

Glu Ala Asn Asp Arg Gly Ala Asn Tyr Pro Phe Leu Thr Asp Gly Asp
        195                 200                 205

Gly Asn Ile Thr Glu Gly Ser Gly Phe Asn Ile Val Leu Ile Lys Asp
    210                 215                 220

Arg Val Leu Tyr Thr Pro Ala Arg Gly Val Leu Glu Gly Val Thr Arg
225                 230                 235                 240

Lys Ser Val Phe Asp Val Ala Asn Lys Leu Gly Leu Glu Val Arg Leu
                245                 250                 255

Asp Phe Val Pro Val Glu Leu Ala Tyr His Cys Asp Glu Met Phe Met
            260                 265                 270

Cys Thr Thr Ala Gly Gly Ile Met Pro Ile Thr Ser Leu Asp Gly Val
        275                 280                 285

Pro Val Gln Asp Gly Lys Val Gly Pro Leu Thr Ala Lys Ile Trp Asp
    290                 295                 300

Leu Tyr Trp Asp Met His Tyr Asp Asp Thr Tyr Ser Phe Ala Ile Asp
305                 310                 315                 320

Tyr Asp Gly Val Glu Gly Lys Lys Asn Gly Val Asn Gly Val Asn Gly
                325                 330                 335

Thr Asn Gly Val Ala His
            340


<210> SEQ ID NO 7
<211> LENGTH: 402
<212> TYPE: PRT
<213> ORGANISM: Klebsiella pneumoniae subsp. pneumoniae Ecl8

<400> SEQUENCE: 7

Met Met Ser Gly Ser Met Thr Arg Glu Asp Phe Asp Ala Tyr Leu Val
1               5                   10                  15

Pro Cys Phe Ala Pro Ala Pro Phe Ile Pro Val Arg Ala Ala Gly Ser
            20                  25                  30

Arg Val Trp Asp Gln Gln Gly Lys Glu Tyr Ile Asp Met Ala Gly Gly
        35                  40                  45

Ile Ala Val Asn Ala Leu Gly His Ala His Pro Ala Leu Ala Gln Ala
    50                  55                  60

Leu Gln Asp Gln Leu Ala Lys Leu Trp His Ile Gly Asn Gly Tyr Thr
65                  70                  75                  80

Asn Glu Pro Val Leu Gln Leu Ala Lys Thr Leu Val Gln Ser Thr Phe
                85                  90                  95

Ala Asp Lys Val Phe Phe Cys Asn Ser Gly Ala Glu Ala Asn Glu Ala
            100                 105                 110

Ala Leu Lys Leu Ala Arg Lys Tyr Ala His Asp Lys Phe Gly Gly Glu
        115                 120                 125

Lys Ser Glu Ile Ile Ala Phe Asn His Ala Phe His Gly Arg Thr Leu
    130                 135                 140
```

-continued

```
Phe Thr Val Ser Val Gly Gly Gln Pro Lys Tyr Ser Ser Asp Tyr Ala
145                 150                 155                 160

Pro Leu Pro Gln Gly Ile Thr His Leu Pro Tyr Asn Asp Ile Glu Ala
                165                 170                 175

Val Thr Ala Ala Ile Ser Ser Arg Thr Cys Ala Val Ile Val Glu Pro
            180                 185                 190

Ile Ile Gly Glu Gly Gly Val Ile Pro Ala Asp Pro Ala Phe Leu Gln
        195                 200                 205

Ala Leu Arg Thr Leu Cys Asp Arg His His Ala Thr Leu Ile Phe Asp
    210                 215                 220

Glu Val Gln Thr Gly Ala Gly Arg Thr Gly His Leu Tyr Ala Tyr Gln
225                 230                 235                 240

His Tyr Asn Val Val Pro Asp Ile Leu Thr Ser Ala Lys Gly Leu Gly
                245                 250                 255

Gly Gly Phe Pro Ile Gly Ala Met Leu Ala Lys Glu Ala Trp Ala Gln
            260                 265                 270

Val Phe Gln Pro Gly Thr His Gly Thr Thr Phe Gly Gly Asn Pro Leu
        275                 280                 285

Ala Ala Thr Val Ala Asn Ala Val Leu Ala His Leu Asp Ala Pro Leu
    290                 295                 300

Leu Ala Gly Val Gly Glu Arg His Ala Leu Ile Val Asp Gln Leu Asn
305                 310                 315                 320

Ala Ile Ser Ala Arg Tyr Asp Ala Phe Ser Ala Val Arg Gly Thr Gly
                325                 330                 335

Leu Leu Ile Gly Ala Glu Leu Ala Gly Pro Leu Arg Gly Lys Ala Lys
            340                 345                 350

Thr Leu Thr Asn Leu Ala Ala Glu Glu Gly Leu Ile Ala Leu Ile Ala
        355                 360                 365

Gly Pro Asp Val Leu Arg Phe Ala Pro Ala Leu Asn Ile Pro Leu Ala
    370                 375                 380

Asp Ile Ala Glu Ala Phe Val Arg Leu Asp Arg Ala Val Ala Arg Leu
385                 390                 395                 400

Thr Arg


<210> SEQ ID NO 8
<211> LENGTH: 310
<212> TYPE: PRT
<213> ORGANISM: Mycobacterium goodii

<400> SEQUENCE: 8

Met Arg Tyr Ser Asp Tyr Glu Leu Asp Glu Ser Ser Pro Phe Ala Gly
1               5                   10                  15

Gly Val Ala Trp Ile Glu Gly Glu Tyr Val Pro Ala Ser Glu Ala Arg
            20                  25                  30

Ile Ser Leu Phe Asp Thr Gly Phe Gly His Ser Asp Leu Thr Tyr Thr
        35                  40                  45

Val Ala His Val Trp His Gly Asn Val Phe Arg Leu His Asp His Met
    50                  55                  60

Asp Arg Leu Tyr Asp Gly Ala Ala Lys Leu Arg Leu Asp Pro Gly Met
65                  70                  75                  80

Ser Lys Leu Glu Met Ala Glu Ile Gly Lys Lys Cys Val Ser Leu Ser
                85                  90                  95

Gln Leu Arg Glu Ser Phe Leu Asn Phe Thr Ile Thr Arg Gly Tyr Gly
            100                 105                 110
```

```
Lys Arg Arg Gly Glu Lys Asp Leu Thr Gln Leu Thr His Gln Val Tyr
        115                 120                 125

Val Tyr Ala Ile Pro Tyr Leu Trp Val Phe Pro Pro Leu Glu Gln Met
    130                 135                 140

Tyr Gly Thr Ser Ala Ile Val Pro Arg His Val Arg Arg Ala Gly Arg
145                 150                 155                 160

Asn Thr Ile Asp Pro Ser Ile Lys Asn Tyr Gln Trp Gly Asp Leu Thr
                165                 170                 175

Ala Ala Ser Phe Glu Ala Lys Asp Arg Gly Ala Arg Thr Ala Val Leu
            180                 185                 190

Leu Asp Ala Asp Asn Cys Val Ala Glu Gly Pro Gly Phe Asn Val Cys
        195                 200                 205

Ile Val Lys Asp Gly Lys Ile Ala Ser Pro Ser Arg Asn Ala Leu Pro
    210                 215                 220

Gly Ile Thr Arg Lys Thr Val Leu Glu Ile Ala Glu Gln Met Gly Ile
225                 230                 235                 240

Glu Ala Thr Leu Arg Asp Val Thr Ser His Glu Leu Tyr Glu Ala Asp
                245                 250                 255

Glu Leu Ile Ala Cys Thr Thr Ala Gly Gly Val Thr Pro Ile Thr Ser
            260                 265                 270

Leu Asp Gly Glu Pro Ile Gly Asn Gly Glu Pro Gly Pro Ile Thr Val
        275                 280                 285

Ala Ile Arg Asp Arg Phe Trp Ala Leu Met Asp Glu Pro Gly Pro Leu
    290                 295                 300

Ile Glu Ala Ile Asp Tyr
305                 310


<210> SEQ ID NO 9
<211> LENGTH: 394
<212> TYPE: PRT
<213> ORGANISM: Paracoccus denitrificans

<400> SEQUENCE: 9

Met Leu Gly Asn Leu Lys Pro Gln Ala Pro Asp Lys Ile Leu Ala Leu
1               5                   10                  15

Met Gly Glu Phe Arg Ala Asp Pro Arg Gln Gly Lys Ile Asp Leu Gly
            20                  25                  30

Val Gly Val Tyr Lys Asp Ala Thr Gly His Thr Pro Ile Met Arg Ala
        35                  40                  45

Val His Ala Ala Glu Gln Arg Met Leu Glu Thr Glu Thr Thr Lys Thr
    50                  55                  60

Tyr Ala Gly Leu Ser Gly Glu Pro Glu Phe Gln Lys Ala Met Gly Glu
65                  70                  75                  80

Leu Ile Leu Gly Asp Gly Leu Lys Ser Glu Thr Thr Ala Thr Leu Ala
                85                  90                  95

Thr Val Gly Gly Thr Gly Ala Leu Arg Gln Ala Leu Glu Leu Ala Arg
            100                 105                 110

Met Ala Asn Pro Asp Leu Arg Val Phe Val Ser Asp Pro Thr Trp Pro
        115                 120                 125

Asn His Val Ser Ile Met Asn Phe Met Gly Leu Pro Val Gln Thr Tyr
    130                 135                 140

Arg Tyr Phe Asp Ala Glu Thr Arg Gly Val Asp Phe Glu Gly Met Lys
145                 150                 155                 160

Ala Asp Leu Ala Ala Ala Lys Lys Gly Asp Met Val Leu Leu His Gly
                165                 170                 175
```

```
Cys Cys His Asn Pro Thr Gly Ala Asn Leu Thr Leu Asp Gln Trp Ala
            180                 185                 190

Glu Ile Ala Ser Ile Leu Glu Lys Thr Gly Ala Leu Pro Leu Ile Asp
        195                 200                 205

Leu Ala Tyr Gln Gly Phe Gly Asp Gly Leu Glu Glu Asp Ala Ala Gly
    210                 215                 220

Thr Arg Leu Ile Ala Ser Arg Ile Pro Glu Val Leu Ile Ala Ala Ser
225                 230                 235                 240

Cys Ser Lys Asn Phe Gly Ile Tyr Arg Glu Arg Thr Gly Cys Leu Leu
                245                 250                 255

Ala Leu Cys Ala Asp Ala Ala Thr Arg Glu Leu Ala Gln Gly Ala Met
            260                 265                 270

Ala Phe Leu Asn Arg Gln Thr Tyr Ser Phe Pro Pro Phe His Gly Ala
        275                 280                 285

Lys Ile Val Ser Thr Val Leu Thr Thr Pro Glu Leu Arg Ala Asp Trp
    290                 295                 300

Met Ala Glu Leu Glu Ala Val Arg Ser Gly Met Leu Arg Leu Arg Glu
305                 310                 315                 320

Gln Leu Ala Gly Glu Leu Arg Asp Leu Ser Gly Ser Asp Arg Phe Gly
                325                 330                 335

Phe Val Ala Glu His Arg Gly Met Phe Ser Arg Leu Gly Ala Thr Pro
            340                 345                 350

Glu Gln Val Lys Arg Ile Lys Glu Glu Phe Gly Ile Tyr Met Val Gly
        355                 360                 365

Asp Ser Arg Ile Asn Ile Ala Gly Leu Asn Asp Asn Thr Ile Pro Ile
    370                 375                 380

Leu Ala Arg Ala Ile Ile Glu Val Gly Val
385                 390
```

<210> SEQ ID NO 10
<211> LENGTH: 336
<212> TYPE: PRT
<213> ORGANISM: Penicillium brasilianum

<400> SEQUENCE: 10

```
Met Ser Ser Met Asp Gln Val Phe Ala Gly Tyr Ala Ala Arg Thr Ala
1               5                   10                  15

Ala Leu Lys Ala Asn Ser Asn Pro Phe Ala Lys Gly Ile Ala Trp Val
            20                  25                  30

Glu Gly Arg Leu Val Pro Ile Asn Glu Ala Arg Ile Pro Leu Met Asp
        35                  40                  45

Gln Gly Phe Leu His Gly Asp Leu Thr Tyr Asp Val Pro Ser Ile Trp
    50                  55                  60

Asp Gly Arg Phe Phe Arg Leu Asp Asp His Leu Ser Arg Leu Glu Ala
65                  70                  75                  80

Ser Cys His Lys Leu Arg Met Arg Leu Pro Leu Pro Lys Glu His Ile
                85                  90                  95

Glu Leu Ile Leu Asn Glu Met Ala Ala Lys Cys Gly Ile Lys Asp Ala
            100                 105                 110

Tyr Val Glu Leu Ile Val Thr Arg Gly Leu Thr Gly Val Arg Gly Ser
        115                 120                 125

Asn Pro Asp Gln Leu Arg Lys Asn Thr Leu Tyr Met Phe Ile Leu Pro
    130                 135                 140

Tyr Val Trp Val Met Glu Pro Gln Val Gln Arg Thr Gly Gly Ser Ala
```

```
145                 150                 155                 160

Val Val Ala Arg Thr Val Arg Arg Thr Pro Val Gly Ser Met Asp Pro
                165                 170                 175

Thr Val Lys Asn Leu Gln Trp Gly Asp Leu Thr Arg Gly Met Leu Glu
            180                 185                 190

Ala Ala Asp Arg Gly Ala Met His Pro Leu Leu Thr Asp Gly Asp Gly
        195                 200                 205

Asn Leu Thr Glu Gly Ser Gly Phe Asn Ile Val Leu Val Lys Asp Gly
    210                 215                 220

Val Leu Phe Thr Pro Glu Arg Gly Val Leu Glu Gly Val Thr Arg Lys
225                 230                 235                 240

Ser Val Leu Glu Ile Ala Arg Ala Asn Gly Ile Asp Ala Arg Val Gln
                245                 250                 255

Phe Val Pro Val Glu Met Leu Tyr His Cys Asp Glu Leu Phe Met Cys
            260                 265                 270

Thr Thr Ala Gly Gly Ile Met Pro Ile Thr Ser Leu Asp Gly Lys Pro
        275                 280                 285

Val Lys Asp Gly Lys Ile Gly Pro Ile Thr Lys His Ile Trp Asp Asp
    290                 295                 300

Tyr Trp Ala Met His Tyr Asp Ser Arg His Ser Tyr Ala Ile Asp Tyr
305                 310                 315                 320

Ala Gly Ser Gly Leu Gln Ser Ser Gly Thr Ala Arg Val Gln Lys Leu
                325                 330                 335


<210> SEQ ID NO 11
<211> LENGTH: 309
<212> TYPE: PRT
<213> ORGANISM: Enterobacter sp. TL3

<400> SEQUENCE: 11

Met Thr Thr Lys Lys Ala Asp Tyr Ile Trp Phe Asn Gly Glu Met Val
1               5                   10                  15

Arg Trp Glu Asp Ala Lys Val His Val Met Ser His Ala Leu His Tyr
            20                  25                  30

Gly Thr Ser Val Phe Glu Gly Ile Arg Cys Tyr Asp Ser His Lys Gly
        35                  40                  45

Pro Val Val Phe Arg His Arg Glu His Met Gln Arg Leu His Asp Ser
    50                  55                  60

Ala Lys Ile Tyr Arg Phe Pro Val Ser Gln Ser Val Asp Glu Leu Met
65                  70                  75                  80

Glu Ala Cys Arg Glu Val Ile Arg Lys Asn Asn Leu Thr Ser Ala Tyr
                85                  90                  95

Ile Arg Pro Leu Val Phe Val Gly Asp Val Gly Met Gly Val Asn Pro
            100                 105                 110

Pro Ala Gly Tyr Asn Thr Asp Val Ile Ile Ala Ala Phe Pro Trp Gly
        115                 120                 125

Ala Tyr Leu Gly Ala Glu Ala Leu Glu Gln Gly Ile Asp Ala Met Val
    130                 135                 140

Ser Ser Trp Asn Arg Val Ala Pro Asn Thr Ile Pro Thr Ala Ala Lys
145                 150                 155                 160

Ala Gly Gly Asn Tyr Leu Ser Ser Leu Leu Val Gly Ser Glu Ala Arg
                165                 170                 175

Arg His Gly Tyr Gln Glu Gly Ile Ala Leu Asp Val Asn Gly Tyr Ile
            180                 185                 190
```

```
Ser Glu Gly Ala Gly Glu Asn Leu Phe Glu Val Lys Asp Gly Ile Leu
        195                 200                 205

Phe Thr Pro Pro Phe Thr Ser Ser Ala Leu Pro Gly Ile Thr Arg Asp
    210                 215                 220

Ala Ile Ile Lys Leu Ala Lys Asp Leu Gly Ile Glu Val Arg Glu Gln
225                 230                 235                 240

Val Leu Ser Arg Glu Ser Leu Tyr Leu Ala Asp Glu Val Phe Met Ser
                245                 250                 255

Gly Thr Ala Ala Glu Ile Thr Pro Val Arg Ser Val Asp Gly Ile Gln
            260                 265                 270

Val Gly Glu Gly Arg Cys Gly Pro Val Thr Lys Arg Ile Gln Gln Ala
        275                 280                 285

Phe Phe Gly Leu Phe Thr Gly Glu Thr Glu Asp Lys Tyr Gly Trp Leu
    290                 295                 300

Asp Gln Val Asn His
305


<210> SEQ ID NO 12
<211> LENGTH: 325
<212> TYPE: PRT
<213> ORGANISM: Aspergillus terreus NIH2624

<400> SEQUENCE: 12

Met Ala Ser Met Asp Lys Val Phe Ala Gly Tyr Ala Ala Arg Gln Ala
1               5                   10                  15

Ile Leu Glu Ser Thr Glu Thr Thr Asn Pro Phe Ala Lys Gly Ile Ala
            20                  25                  30

Trp Val Glu Gly Glu Leu Val Pro Leu Ala Glu Ala Arg Ile Pro Leu
        35                  40                  45

Leu Asp Gln Gly Phe Met His Ser Asp Leu Thr Tyr Asp Val Pro Ser
    50                  55                  60

Val Trp Asp Gly Arg Phe Phe Arg Leu Asp Asp His Ile Thr Arg Leu
65                  70                  75                  80

Glu Ala Ser Cys Thr Lys Leu Arg Leu Arg Leu Pro Leu Pro Arg Asp
                85                  90                  95

Gln Val Lys Gln Ile Leu Val Glu Met Val Ala Lys Ser Gly Ile Arg
            100                 105                 110

Asp Ala Phe Val Glu Leu Ile Val Thr Arg Gly Leu Lys Gly Val Arg
        115                 120                 125

Gly Thr Arg Pro Glu Asp Ile Val Asn Asn Leu Tyr Met Phe Val Gln
    130                 135                 140

Pro Tyr Val Trp Val Met Glu Pro Asp Met Gln Arg Val Gly Gly Ser
145                 150                 155                 160

Ala Val Val Ala Arg Thr Val Arg Arg Val Pro Pro Gly Ala Ile Asp
                165                 170                 175

Pro Thr Val Lys Asn Leu Gln Trp Gly Asp Leu Val Arg Gly Met Phe
            180                 185                 190

Glu Ala Ala Asp Arg Gly Ala Thr Tyr Pro Phe Leu Thr Asp Gly Asp
        195                 200                 205

Ala His Leu Thr Glu Gly Ser Gly Phe Asn Ile Val Leu Val Lys Asp
    210                 215                 220

Gly Val Leu Tyr Thr Pro Asp Arg Gly Val Leu Gln Gly Val Thr Arg
225                 230                 235                 240

Lys Ser Val Ile Asn Ala Ala Glu Ala Phe Gly Ile Glu Val Arg Val
                245                 250                 255
```

```
Glu Phe Val Pro Val Glu Leu Ala Tyr Arg Cys Asp Glu Ile Phe Met
            260                 265                 270

Cys Thr Thr Ala Gly Gly Ile Met Pro Ile Thr Thr Leu Asp Gly Met
        275                 280                 285

Pro Val Asn Gly Gly Gln Ile Gly Pro Ile Thr Lys Lys Ile Trp Asp
    290                 295                 300

Gly Tyr Trp Ala Met His Tyr Asp Ala Ala Tyr Ser Phe Glu Ile Asp
305                 310                 315                 320

Tyr Asn Glu Arg Asn
                325


<210> SEQ ID NO 13
<211> LENGTH: 325
<212> TYPE: PRT
<213> ORGANISM: Exophiala spinifera

<400> SEQUENCE: 13

Met Ala Phe Met Asp Lys Val Phe Gly Ala Tyr Asp Arg Arg Thr Ala
1               5                   10                  15

Thr Leu Thr Lys Thr Asp Asn Pro Phe Ala Lys Gly Ala Ala Trp Val
            20                  25                  30

Glu Gly Val Val Val Pro Leu His Glu Ala Arg Ile Pro Leu Leu Asp
        35                  40                  45

Gln Gly Phe Leu His Ser Asp Leu Thr Tyr Asp Val Pro Ala Val Trp
    50                  55                  60

Asp Gly Arg Tyr Phe Arg Leu Asp Asp His Leu Thr Arg Phe Glu Ala
65                  70                  75                  80

Ser Leu Val Lys Met Arg Leu Thr Leu Pro Leu Pro Arg Ala Glu Val
                85                  90                  95

Arg Ala Ile Met Val Asp Met Val Ala Arg Ser Gly Ile Arg Asp Val
            100                 105                 110

Phe Val Glu Ile Ile Val Thr Arg Gly Leu Gln Phe Val Arg Gly Thr
        115                 120                 125

Pro Leu Glu Ser His Ile His Asn Leu Tyr Ile Leu Ile Met Pro Tyr
    130                 135                 140

Ile Trp Ala Met Pro Pro Glu Ile Gln Arg Thr Gly Gly Ser Ala Ile
145                 150                 155                 160

Val Ala Arg Thr Val Arg Arg Thr Pro Pro Gly Ser Met Asp Pro Thr
                165                 170                 175

Ile Lys Asn Leu Gln Trp Gly Asp Leu Thr Arg Ala Leu Leu Glu Ser
            180                 185                 190

His Asp Arg Gly Ala Leu His Pro Phe Leu Thr Asp Gly Asp Ala Asn
        195                 200                 205

Leu Thr Glu Gly Pro Gly Tyr Asn Ile Ile Leu Ile Lys Asp Gly Val
    210                 215                 220

Leu Tyr Thr Pro Asp Arg Gly Val Leu Glu Gly Val Thr Arg Lys Ser
225                 230                 235                 240

Val Met Glu Ile Ala Arg Ala Asn Gly Ile Glu Val Arg Lys Gln Val
                245                 250                 255

Val Pro Val Glu Leu Ala Tyr Gln Ala Asp Glu Ile Phe Thr Cys Thr
            260                 265                 270

Thr Ala Gly Gly Val Met Pro Ile Thr Ser Leu Asp Glu Arg Pro Val
        275                 280                 285

Lys Asp Gly Gln Ile Gly Pro Ile Thr Arg Ile Ile Trp Glu Glu Tyr
```

-continued

```
    290                 295                 300

Trp Glu Met His Tyr Asn Pro Gln Tyr Ser Phe Val Val Glu Tyr Asp
305                 310                 315                 320

Asn Arg Ser His Leu
                325


<210> SEQ ID NO 14
<211> LENGTH: 415
<212> TYPE: PRT
<213> ORGANISM: Deinococcus geothermalis

<400> SEQUENCE: 14

Met Thr Gly Thr Lys Thr Lys Ala Ser Lys Trp Leu Asp Ala Glu Leu
1               5                   10                  15

Arg Tyr Asp Ser Gly Val Tyr Asn Lys His Gln Val Val Met Val Arg
            20                  25                  30

Gly Gln Gly Ala Thr Val Trp Asp Glu Thr Gly Arg Ala Tyr Ile Asp
        35                  40                  45

Cys Val Ala Gly Tyr Gly Val Ala Asn Ile Gly His Cys His Pro Asp
    50                  55                  60

Val Val Lys Ala Ile Gln Glu Gln Ala Ala Arg Leu Ile Val Met Pro
65                  70                  75                  80

Gln Thr Leu Pro Asn Asp Lys Arg Ala Glu Phe Leu Thr Glu Leu Val
                85                  90                  95

Gly Val Leu Pro Gln Gly Leu Glu Arg Val Phe Leu Cys Asn Ser Gly
            100                 105                 110

Thr Glu Ala Met Glu Ala Ala Lys Lys Phe Ala Ile Thr Ala Thr Gly
        115                 120                 125

Arg Ser Arg Phe Val Ser Met Lys Arg Gly Phe Ser Gly Arg Ser Leu
    130                 135                 140

Gly Ala Leu Ala Phe Thr Trp Glu Pro Lys Tyr Arg Glu Pro Phe Gly
145                 150                 155                 160

Glu Ala Val Asp Asn Lys His Val Asp Phe Val Thr Tyr Gly Asn Ile
                165                 170                 175

Asp Glu Leu Arg Ala Ala Val Thr Asp Gln Thr Ala Ala Val Ile Leu
            180                 185                 190

Glu Pro Val Gln Gly Glu Gly Gly Val Arg Pro Val Thr Pro Glu Phe
        195                 200                 205

Ile Arg Ala Ala Arg Glu Ile Thr Arg Glu Lys Gly Ala Leu Leu Ile
    210                 215                 220

Leu Asp Glu Ile Gln Thr Gly Phe Cys Arg Thr Gly Lys Met Phe Ala
225                 230                 235                 240

Ala Glu His Phe Gly Val Val Pro Asp Gly Met Thr Leu Ala Lys Ala
                245                 250                 255

Met Ala Gly Gly Val Pro Val Gly Ala Phe Ala Met Thr Ala Glu Val
            260                 265                 270

Ala Asp Arg Met Pro Ala Gly Gly His Gly Thr Thr Phe Gly Gly Asn
        275                 280                 285

Pro Leu Ala Met Ala Ala Gly Ile Ala Ala Ile Arg Ala Met Lys Asn
    290                 295                 300

Glu Lys Met Ala Glu Gln Ala Arg Glu Lys Gly Ala Tyr Phe Met Glu
305                 310                 315                 320

Arg Leu Arg Ala Ile Arg Ser Pro Lys Ile Arg Glu Val Arg Gly Leu
                325                 330                 335
```

```
Gly Leu Met Ile Gly Val Glu Leu Lys Glu Lys Ser Ala Pro Tyr Ile
            340                 345                 350

Ala Ala Leu Glu His Glu Glu Gly Val Leu Thr Leu Ala Ala Thr Pro
        355                 360                 365

Leu Val Val Arg Phe Leu Pro Pro Leu Thr Ile Ser Arg Glu Gln Ile
    370                 375                 380

Asp Gln Val Val Ala Ala Phe Glu Arg Val Leu Glu Arg Val Asn Pro
385                 390                 395                 400

Arg Ala Ile Pro Asn Gln Glu Leu Arg Glu Asp Lys Gln Thr Glu
                405                 410                 415


<210> SEQ ID NO 15
<211> LENGTH: 487
<212> TYPE: PRT
<213> ORGANISM: Geomyces destructans 20631-21

<400> SEQUENCE: 15

Met Ser Thr Ser Pro Arg Leu Arg Ser Leu Asn Ile Asp Asn Ile Asn
1               5                   10                  15

Pro His Val Arg Lys Ala Glu Tyr Ala Val Arg Gly Glu Leu Ala Val
            20                  25                  30

Lys Ser Glu Glu Tyr Arg Ala Gln Leu Ala Ser Gly Lys Gly Ser Asp
        35                  40                  45

Leu Pro Phe Asp Asp Val Ile Ser Ala Asn Ile Gly Asn Pro Gln Gln
    50                  55                  60

Leu Asp Gln Lys Pro Ile Thr Phe Phe Arg Gln Val Leu Ser Leu Leu
65                  70                  75                  80

Glu Tyr Pro Pro Leu Leu Glu Lys Glu Asp Val Leu Leu Asn Gln Leu
                85                  90                  95

Gly Tyr Lys Lys Asp Val Ile Glu Arg Ala Lys Trp Leu Leu Glu Gln
            100                 105                 110

Val Gly Ser Val Gly Ala Tyr Ser Ala Ser Thr Gly Pro Gln Gly Ile
        115                 120                 125

Lys Glu Ser Ile Ala Lys Phe Ile Glu Lys Arg Asp Gly His Pro Ala
    130                 135                 140

Asp Pro Ser Ser Ile Tyr Leu Ser Ala Gly Ala Ser Ser Gly Val Asn
145                 150                 155                 160

Thr Leu Leu His Ile Ile Cys Ala Gly Pro Lys Thr Gly Ile Leu Val
                165                 170                 175

Pro Ile Pro Gln Tyr Pro Leu Tyr Thr Ala Thr Leu Ser Leu Leu Asp
            180                 185                 190

Ala Thr Cys Val Pro Tyr Tyr Leu Asp Glu Ala Asn Ala Trp Ser Thr
        195                 200                 205

Ser Ala Glu Ser Ile Thr Ser Ala Leu Thr Thr Ala Lys Glu Ala Gly
    210                 215                 220

Thr Asp Val Arg Ala Ile Ala Ile Ile Asn Pro Gly Asn Pro Thr Gly
225                 230                 235                 240

Ala Ser Leu Ser Tyr Lys Asp Ile Glu Ser Val Ile Asp Leu Ala Ala
                245                 250                 255

Ser Glu His Leu Val Ile Leu Ala Asp Glu Val Tyr Gln Thr Asn Val
            260                 265                 270

Phe Ile Gly Lys Phe His Ser Phe Lys Ala Val Leu Arg Asp Met Gln
        275                 280                 285

Lys Lys Asn Pro Gly Lys Tyr Asp Thr Val Glu Leu Val Ser Leu His
    290                 295                 300
```

```
Ser Val Ser Lys Gly Ile Val Gly Glu Cys Gly His Arg Gly Gly Tyr
305                 310                 315                 320

Phe Glu Leu Cys Gly Phe Asp Pro Glu Val Val Ala Gln Ile Tyr Lys
                325                 330                 335

Phe Val Ser Ile Ser Leu Cys Ala Pro Val Ile Gly Gln Cys Leu Val
            340                 345                 350

Glu Leu Met Val Asn Pro Pro Thr Glu Gly Glu Pro Ser Tyr Asp Leu
        355                 360                 365

Tyr Lys Ser Glu Arg Asp Gly Ile Phe Ala Gly Leu Gln Ser Arg Ala
    370                 375                 380

Thr Ala Leu His Lys Ala Phe Gln Ala Met Glu Gly Val Glu Cys Gly
385                 390                 395                 400

Pro Pro Gln Gly Ser Met Tyr Leu Phe Pro Ser Ile Thr Leu Pro Gln
                405                 410                 415

Lys Ala Ile Glu Ala Ala Lys Ala Asp Gly Lys Thr Pro Asp Ala Phe
            420                 425                 430

Tyr Ala Met Lys Met Leu Glu Ala Thr Gly Val Cys Val Val Pro Gly
        435                 440                 445

Ala Gly Phe Gly Gln Lys Glu Gly Thr Leu His Phe Arg Thr Thr Phe
    450                 455                 460

Leu Ala Pro Gly Thr Ser Trp Val Glu Gly Val Ala Arg Phe His Glu
465                 470                 475                 480

Gly Phe Met Gly Glu Tyr Arg
                485


<210> SEQ ID NO 16
<211> LENGTH: 470
<212> TYPE: PRT
<213> ORGANISM: Pseudomonas putida KT2440

<400> SEQUENCE: 16

Met Ala Thr Pro Ser Lys Ala Phe Ala Ile Ala His Asp Pro Leu Val
1               5                   10                  15

Glu Ala Asp Lys Ala His Tyr Met His Gly Tyr His Val Phe Asp Glu
            20                  25                  30

His Arg Glu Gln Gly Ala Leu Asn Ile Val Ala Gly Glu Gly Ala Tyr
        35                  40                  45

Ile Arg Asp Thr His Gly Asn Arg Phe Leu Asp Ala Val Gly Gly Met
    50                  55                  60

Trp Cys Thr Asn Ile Gly Leu Gly Arg Glu Glu Met Ala Leu Ala Ile
65                  70                  75                  80

Val Asp Gln Val Arg Gln Leu Ala Tyr Ser Asn Pro Phe Ser Asp Met
                85                  90                  95

Ala Asn Asp Val Ala Ile Glu Leu Cys Gln Lys Leu Ala Gln Leu Ala
            100                 105                 110

Pro Gly Asp Leu Asn His Val Phe Leu Thr Thr Gly Gly Ser Thr Ala
        115                 120                 125

Val Asp Thr Ala Tyr Arg Leu Ile Gln Tyr Tyr Gln Asn Cys Arg Gly
    130                 135                 140

Lys Pro His Lys Lys His Ile Ile Ala Arg Tyr Asn Ala Tyr His Gly
145                 150                 155                 160

Ser Thr Thr Leu Thr Met Ser Ile Gly Asn Lys Ala Ala Asp Arg Val
                165                 170                 175

Pro Glu Phe Asp Tyr His His Asp Leu Ile His His Val Ser Asn Pro
```

```
            180                 185                 190

Asn Pro Tyr Arg Ala Pro Asp Asp Met Asp Glu Ala Glu Phe Leu Asp
        195                 200                 205

Phe Leu Val Ala Glu Phe Glu Asp Lys Ile Leu Ser Leu Gly Ala Asp
    210                 215                 220

Asn Val Ala Ala Phe Phe Ala Glu Pro Ile Met Gly Ser Gly Gly Val
225                 230                 235                 240

Ile Ile Pro Pro Glu Gly Tyr Phe Gln Arg Met Trp Gln Leu Cys Gln
                245                 250                 255

Thr Tyr Asp Ile Leu Phe Val Ala Asp Glu Val Val Thr Ser Phe Gly
            260                 265                 270

Arg Leu Gly Thr Phe Phe Ala Ser Glu Glu Leu Phe Gly Val Thr Pro
        275                 280                 285

Asp Ile Ile Thr Thr Ala Lys Gly Leu Thr Ser Ala Tyr Leu Pro Leu
    290                 295                 300

Gly Ala Cys Ile Phe Ser Glu Arg Ile Trp Gln Val Ile Ala Glu Pro
305                 310                 315                 320

Gly Lys Gly Arg Cys Phe Thr His Gly Phe Thr Tyr Ser Gly His Pro
                325                 330                 335

Val Cys Cys Thr Ala Ala Leu Lys Asn Ile Glu Ile Ile Glu Arg Glu
            340                 345                 350

Gln Leu Leu Asp His Val Asn Asp Val Gly Ser Tyr Leu Glu Gln Arg
        355                 360                 365

Leu Gln Ser Leu Arg Asp Leu Pro Leu Val Gly Asp Val Arg Cys Met
    370                 375                 380

Lys Leu Met Ala Cys Val Glu Phe Val Ala Asn Lys Ala Ser Lys Ala
385                 390                 395                 400

Leu Phe Ala Asp Glu Val Asn Ile Gly Glu Arg Ile His Ser Lys Ala
                405                 410                 415

Gln Glu Lys Gly Leu Leu Val Arg Pro Ile Met His Leu Asn Val Met
            420                 425                 430

Ser Pro Pro Leu Ile Ile Thr His Ala Gln Val Asp Glu Ile Val Glu
        435                 440                 445

Thr Leu Arg Gln Cys Ile Ile Glu Thr Ala Arg Glu Leu Thr Ala Leu
    450                 455                 460

Gly Leu Tyr Gln Gly Arg
465                 470


<210> SEQ ID NO 17
<211> LENGTH: 283
<212> TYPE: PRT
<213> ORGANISM: Lysinibacillus sphaericus

<400> SEQUENCE: 17

Met Ala Tyr Ser Leu Trp Asn Asp Gln Ile Val Glu Glu Gly Ser Ile
1               5                   10                  15

Thr Ile Ser Pro Glu Asp Arg Gly Tyr Gln Phe Gly Asp Gly Ile Tyr
            20                  25                  30

Glu Val Ile Lys Val Tyr Asn Gly His Met Phe Thr Ala Gln Glu His
        35                  40                  45

Ile Asp Arg Phe Tyr Ala Ser Ala Glu Lys Ile Arg Leu Val Ile Pro
    50                  55                  60

Tyr Thr Lys Asp Val Leu His Lys Leu Leu His Asp Leu Ile Glu Lys
65                  70                  75                  80
```

-continued

Asn Asn Leu Asn Thr Gly His Val Tyr Phe Gln Ile Thr Arg Gly Thr
85 90 95

Thr Ser Arg Asn His Ile Phe Pro Asp Ala Ser Val Pro Ala Val Leu
100 105 110

Thr Gly Asn Val Lys Thr Gly Glu Arg Ser Ile Glu Asn Phe Glu Lys
115 120 125

Gly Val Lys Ala Thr Leu Val Glu Asp Val Arg Trp Leu Arg Cys Asp
130 135 140

Ile Lys Ser Leu Asn Leu Leu Gly Ala Val Leu Ala Lys Gln Glu Ala
145 150 155 160

Ser Glu Lys Gly Cys Tyr Glu Ala Ile Leu His Arg Gly Asp Ile Ile
165 170 175

Thr Glu Cys Ser Ser Ala Asn Val Tyr Gly Ile Lys Asp Gly Lys Leu
180 185 190

Tyr Thr His Pro Ala Asn Asn Tyr Ile Leu Asn Gly Ile Thr Arg Gln
195 200 205

Val Ile Leu Lys Cys Ala Ala Glu Ile Asn Leu Pro Val Ile Glu Glu
210 215 220

Pro Met Thr Lys Gly Asp Leu Leu Thr Met Asp Glu Ile Ile Val Ser
225 230 235 240

Ser Val Ser Ser Glu Val Thr Pro Val Ile Asp Val Asp Gly Gln Gln
245 250 255

Ile Gly Ala Gly Val Pro Gly Glu Trp Thr Arg Lys Leu Gln Lys Ala
260 265 270

Phe Glu Ala Lys Leu Pro Ile Ser Ile Asn Ala
275 280

<210> SEQ ID NO 18
<211> LENGTH: 390
<212> TYPE: PRT
<213> ORGANISM: Bacillus megaterium DSM 319

<400> SEQUENCE: 18

Met Lys Gln Phe Glu Gln Ser Glu Leu Leu Lys Ser Leu Pro Lys Gln
1 5 10 15

Phe Phe Ala Ser Leu Val Gly Lys Val Gly Lys Val Met Ala Gln Gly
20 25 30

His Asp Val Ile Asn Leu Gly Gln Gly Asn Pro Asp Gln Pro Thr Pro
35 40 45

Ser His Ile Val Glu Thr Leu Gln Lys Ala Ser Ala Asn Pro Met His
50 55 60

His Lys Tyr Ser Pro Phe Arg Gly His Gln Phe Leu Lys Glu Ala Val
65 70 75 80

Ala Thr Phe Tyr Lys Arg Glu Tyr Gly Val Asp Val Asp Pro Glu Lys
85 90 95

Glu Val Ala Ile Leu Phe Gly Gly Lys Gly Gly Leu Val Glu Ile Pro
100 105 110

Gln Cys Leu Leu Asn Pro Gly Asp Thr Val Leu Val Pro Asp Pro Gly
115 120 125

Tyr Pro Asp Tyr Trp Ser Gly Val Glu Leu Ala Lys Ala Lys Met Glu
130 135 140

Val Met Pro Leu Thr Ala Glu Asn His Phe Leu Pro Leu Tyr Glu Glu
145 150 155 160

Ile Ser Glu Arg Thr Lys Glu Gln Ala Lys Leu Met Phe Leu Asn Tyr
165 170 175

```
Pro Asn Asn Pro Thr Gly Ala Val Ala Thr Ala Glu Phe Phe Glu Asp
            180                 185                 190

Thr Val Ala Phe Ala Ala Lys His Asn Ile Cys Val Val His Asp Phe
        195                 200                 205

Ala Tyr Gly Ala Ile Gly Phe Asp Gly Lys Lys Pro Ile Ser Phe Leu
    210                 215                 220

Gln Thr Pro Gly Ala Lys Glu Met Gly Ile Glu Ile Tyr Thr Leu Ser
225                 230                 235                 240

Lys Thr Tyr Asn Met Ala Gly Trp Arg Val Gly Phe Ala Val Gly Asn
                245                 250                 255

Glu Ser Val Val Glu Ala Ile Asn Leu Leu Gln Asp His Met Tyr Val
            260                 265                 270

Ser Leu Phe Gly Ala Val Gln Glu Ala Ala Ala Ala Ala Leu Leu Glu
        275                 280                 285

Ser Gln Gln Cys Val Asn Val Leu Val Lys Arg Tyr Glu Ser Arg Arg
    290                 295                 300

Asn Thr Phe Ile Gln Gly Leu Arg Glu Ile Gly Trp Asp Val Thr Ser
305                 310                 315                 320

Pro Ala Gly Ser Phe Phe Ala Trp Leu Lys Val Pro Glu Gly Tyr Thr
                325                 330                 335

Ser Glu Gln Phe Ser Asp Leu Leu Leu Glu Lys Ala His Val Val Val
            340                 345                 350

Ala Pro Gly Val Gly Phe Gly Thr Tyr Gly Glu Gly Tyr Val Arg Val
        355                 360                 365

Gly Leu Leu Thr Asp Glu Glu Arg Met Arg Glu Ala Val Ser Arg Ile
    370                 375                 380

Lys Lys Leu Asn Leu Phe
385                 390
```

<210> SEQ ID NO 19
<211> LENGTH: 320
<212> TYPE: PRT
<213> ORGANISM: Trichoderma harzianum

<400> SEQUENCE: 19

```
Met Ala Thr Met Asp Lys Val Phe Ala Gly Tyr Ala Lys Arg Gln Ala
1               5                   10                  15

Ile Leu Glu Ala Ser Asp Asn Pro Leu Ala Arg Gly Val Ala Trp Val
            20                  25                  30

Glu Gly Glu Leu Val Pro Leu His Gln Ala Arg Ile Pro Leu Leu Asp
        35                  40                  45

Gln Gly Phe Met His Ser Asp Leu Thr Tyr Asp Val Pro Ser Val Trp
    50                  55                  60

Asp Gly Arg Phe Phe Arg Leu Asp Asp His Leu Asp Arg Leu Glu Ala
65                  70                  75                  80

Ser Cys Lys Lys Met Arg Leu Arg Phe Pro Ile Ala Arg Gln Glu Ile
                85                  90                  95

Lys Arg Ile Leu Val Asp Met Val Ala Lys Ser Gly Ile Lys Asp Ala
            100                 105                 110

Phe Val Glu Leu Ile Val Thr Arg Gly Leu Thr Gly Val Arg Gly Ala
        115                 120                 125

Arg Pro Glu Asp Leu Leu Asn Asn Asn Leu Tyr Met Phe Val Gln Pro
    130                 135                 140

Tyr Val Trp Val Met Asp Pro Glu Val Gln Tyr His Gly Gly His Ala
```

-continued

```
145                 150                 155                 160

Ile Val Ala Arg Thr Val Arg Arg Val Pro Pro Gly Ser Ile Asp Pro
                165                 170                 175

Thr Ile Lys Asn Leu Gln Trp Gly Asp Leu Val Arg Gly Leu Phe Glu
            180                 185                 190

Ala Asn Asp Arg Gly Ala Thr Tyr Pro Phe Leu Thr Asp Gly Asp Ala
        195                 200                 205

Asn Leu Thr Glu Gly Ser Gly Phe Asn Ile Val Ile Ile Lys Asp Gly
    210                 215                 220

Val Leu Tyr Thr Pro Asp Arg Gly Val Leu Gln Gly Ile Thr Arg Lys
225                 230                 235                 240

Ser Val Met Asp Ala Ala Arg Ser Cys Gly Tyr Glu Ile Arg Val Glu
                245                 250                 255

Gln Val Pro Val Glu Ala Thr Tyr Gln Ala Asp Glu Ile Leu Met Cys
            260                 265                 270

Thr Thr Ala Gly Gly Ile Met Pro Ile Thr Thr Leu Asp Asn Lys Leu
        275                 280                 285

Val Asn Asp Gly Lys Val Gly Pro Ile Thr Lys Ala Val Trp Asp Arg
    290                 295                 300

Tyr Trp Ala Met His Trp Glu Asp Glu Phe Ser Phe Lys Ile Glu Tyr
305                 310                 315                 320


<210> SEQ ID NO 20
<211> LENGTH: 323
<212> TYPE: PRT
<213> ORGANISM: Aspergillus fumigatus R-ATAs

<400> SEQUENCE: 20

Met Ala Ser Met Asp Lys Val Phe Ser Gly Tyr Tyr Ala Arg Gln Lys
1               5                   10                  15

Leu Leu Glu Arg Ser Asp Asn Pro Phe Ser Lys Gly Ile Ala Tyr Val
            20                  25                  30

Glu Gly Lys Leu Val Leu Pro Ser Asp Ala Arg Ile Pro Leu Leu Asp
        35                  40                  45

Glu Gly Phe Met His Ser Asp Leu Thr Tyr Asp Val Ile Ser Val Trp
    50                  55                  60

Asp Gly Arg Phe Phe Arg Leu Asp Asp His Leu Gln Arg Ile Leu Glu
65                  70                  75                  80

Ser Cys Asp Lys Met Arg Leu Lys Phe Pro Leu Ala Leu Ser Ser Val
                85                  90                  95

Lys Asn Ile Leu Ala Glu Met Val Ala Lys Ser Gly Ile Arg Asp Ala
            100                 105                 110

Phe Val Glu Val Ile Val Thr Arg Gly Leu Thr Gly Val Arg Gly Ser
        115                 120                 125

Lys Pro Glu Asp Leu Tyr Asn Asn Asn Ile Tyr Leu Leu Val Leu Pro
    130                 135                 140

Tyr Ile Trp Val Met Ala Pro Glu Asn Gln Leu His Gly Gly Glu Ala
145                 150                 155                 160

Ile Ile Thr Arg Thr Val Arg Arg Thr Pro Pro Gly Ala Phe Asp Pro
                165                 170                 175

Thr Ile Lys Asn Leu Gln Trp Gly Asp Leu Thr Lys Gly Leu Phe Glu
            180                 185                 190

Ala Met Asp Arg Gly Ala Thr Tyr Pro Phe Leu Thr Asp Gly Asp Thr
        195                 200                 205
```

-continued

```
Asn Leu Thr Glu Gly Ser Gly Phe Asn Ile Val Leu Val Lys Asn Gly
    210                 215                 220

Ile Ile Tyr Thr Pro Asp Arg Gly Val Leu Arg Gly Ile Thr Arg Lys
225                 230                 235                 240

Ser Val Ile Asp Val Ala Arg Ala Asn Ser Ile Asp Ile Arg Leu Glu
                245                 250                 255

Val Val Pro Val Glu Gln Ala Tyr His Ser Asp Glu Ile Phe Met Cys
            260                 265                 270

Thr Thr Ala Gly Gly Ile Met Pro Ile Thr Leu Leu Asp Gly Gln Pro
        275                 280                 285

Val Asn Asp Gly Gln Val Gly Pro Ile Thr Lys Lys Ile Trp Asp Gly
    290                 295                 300

Tyr Trp Glu Met His Tyr Asn Pro Ala Tyr Ser Phe Pro Val Asp Tyr
305                 310                 315                 320

Gly Ser Gly


<210> SEQ ID NO 21
<211> LENGTH: 450
<212> TYPE: PRT
<213> ORGANISM: Geobacillus thermodenitrificans subsp.
      thermodenitrificans DSM 465

<400> SEQUENCE: 21

Met Lys Thr Glu Gln Ser His Gln Leu Trp Leu Asp Lys Asp Asp Arg
1               5                   10                  15

Tyr Ile Trp His Ser Met Lys Pro Tyr Asn Pro Asn Ala Thr Val Val
            20                  25                  30

Val Thr Glu Ala Lys Gly Cys Trp Val Thr Asp Val Ala Gly Asn Lys
        35                  40                  45

Tyr Leu Asp Ala Met Ala Gly Leu Trp Cys Val Asn Val Gly Tyr Gly
    50                  55                  60

Arg Glu Glu Leu Ala Glu Ala Ala Tyr Glu Gln Leu Lys Thr Leu Pro
65                  70                  75                  80

Tyr Phe Pro Leu Thr Gln Ser His Leu Pro Ala Ile Gln Leu Gly Glu
                85                  90                  95

Lys Leu Asn Glu Leu Leu Gly Asp Glu Tyr Val Ile Phe Phe Ser Asn
            100                 105                 110

Ser Gly Ser Glu Ala Asn Glu Thr Ala Phe Lys Ile Ala Arg Gln Tyr
        115                 120                 125

His Gln Gln Arg Gly Glu Pro His Arg Tyr Lys Ile Ile Ser Arg Tyr
    130                 135                 140

Arg Ala Tyr His Gly Asn Ser Met Gly Ala Leu Ala Ala Thr Gly Gln
145                 150                 155                 160

Ala Gln Arg Lys Tyr Lys Tyr Glu Pro Leu Ala Pro Gly Phe Ile His
                165                 170                 175

Val Pro Pro Pro Asp Arg Tyr Arg Asp Pro Asp Ala Ala Asp Asp Pro
            180                 185                 190

Arg Gln Leu Arg Ala Val Lys Ala Val Asp Asp Val Met Thr Trp Glu
        195                 200                 205

Leu Ser Glu Thr Ile Ala Ala Met Ile Met Glu Pro Ile Ile Thr Gly
    210                 215                 220

Gly Gly Val Leu Met Pro Pro Asp Gly Tyr Met Lys Ala Val Lys Glu
225                 230                 235                 240

Val Cys Glu Lys His Gly Ala Leu Leu Ile Val Asp Glu Val Ile Cys
                245                 250                 255
```

-continued

```
Gly Phe Gly Arg Thr Gly Lys Pro Phe Gly Phe Met His Glu Gly Ile
            260                 265                 270

Lys Pro Asp Ile Ile Thr Met Ala Lys Gly Ile Thr Ser Ala Tyr Leu
        275                 280                 285

Pro Leu Ala Ala Thr Ala Val Arg Lys Glu Ile Tyr Glu Ala Phe Lys
    290                 295                 300

Gly Thr Asp Glu Tyr Asp Tyr Phe Arg His Val Asn Thr Phe Gly Gly
305                 310                 315                 320

His Pro Ala Ser Cys Ala Leu Ala Leu Lys Asn Ile Glu Ile Met Glu
                325                 330                 335

Thr Glu His Leu Phe Asp Arg Ser Arg Glu Ala Gly Glu Trp Leu Leu
            340                 345                 350

Ser Ala Leu Lys Thr Lys Leu Ala Asp His Pro Tyr Val Gly Asp Val
        355                 360                 365

Arg Gly Arg Gly Leu Leu Val Gly Ile Glu Leu Val Ala Asp Gln Thr
    370                 375                 380

Thr Lys Glu Pro Leu Asp Val Ser Leu Val Asn Gln Val Ile Ser Arg
385                 390                 395                 400

Cys Lys Glu His Gly Val Ile Ile Gly Lys Asn Gly Ala Thr Val Ala
                405                 410                 415

Gly Tyr Asn Asn Val Leu Thr Leu Ser Pro Pro Leu Cys Ile Ser Asp
            420                 425                 430

Asp Glu Leu Ser Phe Leu Val Arg Val Leu Thr Glu Ala Leu Ala Gln
        435                 440                 445

Ile Lys
    450


<210> SEQ ID NO 22
<211> LENGTH: 339
<212> TYPE: PRT
<213> ORGANISM: Cladophialophora bantiana CBS 173.52

<400> SEQUENCE: 22

Met Thr Ser Met Asp Lys Val Phe Ala Ala Tyr Glu Ala Arg Lys Ala
1               5                   10                  15

Val Leu Glu Lys Ser Ala Asn Pro Leu Ala Gln Gly Val Ala Trp Val
            20                  25                  30

Glu Gly Leu Met Val Pro Ile His Glu Ala Arg Ile Pro Leu Leu Asp
        35                  40                  45

Gln Gly Phe Leu His Ser Asp Leu Thr Tyr Asp Val Pro Ser Val Trp
    50                  55                  60

Asp Gly Arg Phe Phe Arg Leu Asp Asp His Leu Ser Arg Leu Glu Asn
65                  70                  75                  80

Ser Cys Ala Lys Met Arg Leu Arg Leu Pro Leu Pro Arg Glu Glu Ile
                85                  90                  95

Lys Arg Val Leu Cys Glu Met Val Ala Lys Ser Gly Met Arg Asp Ala
            100                 105                 110

Phe Val Glu Leu Ile Val Thr Arg Gly Leu Lys Gly Val Arg Gly Ala
        115                 120                 125

Ala Gln Pro Glu Asp Leu Ser Asn Asn Leu Tyr Leu Phe Ile Leu Pro
    130                 135                 140

Tyr Ile Trp Val Met Glu Pro Glu Met Gln Arg His Gly Thr Gly Lys
145                 150                 155                 160

Ala Ile Ile Ala Arg Thr Val Arg Arg Thr Pro Pro Gly Cys Met Asp
```

```
                165                 170                 175

Pro Thr Val Lys Asn Leu Gln Trp Gly Asp Leu Thr Arg Gly Met Phe
            180                 185                 190

Glu Ala Ser Asp Arg Gly Ala Asn Tyr Pro Phe Leu Thr Asp Gly Asp
        195                 200                 205

Gly Asn Ile Thr Glu Gly Ser Gly Phe Asn Ile Val Leu Ile Lys Asp
    210                 215                 220

Gly Val Leu Tyr Thr Pro Ala Arg Gly Val Leu Glu Gly Val Thr Arg
225                 230                 235                 240

Lys Ser Val Phe Asp Val Ala Lys Lys Leu Gly Ile Glu Val Arg Leu
                245                 250                 255

Asp Phe Val Pro Val Glu Leu Ala Tyr His Cys Asp Glu Met Phe Met
            260                 265                 270

Cys Thr Thr Ala Gly Gly Ile Met Pro Ile Thr Ser Leu Asp Gly Val
        275                 280                 285

Pro Val Lys Asp Gly Lys Ile Gly Pro Leu Thr Thr Lys Ile Trp Asp
    290                 295                 300

Leu Tyr Trp Asp Met His Tyr Asp Pro Ala Tyr Ser Phe Pro Ile Asp
305                 310                 315                 320

Tyr Ala Tyr Asp Ser Asn Gly Glu Val Lys Lys Asn Gly Val Asn Gly
                325                 330                 335

Thr Ala His


<210> SEQ ID NO 23
<211> LENGTH: 384
<212> TYPE: PRT
<213> ORGANISM: Bacillus megaterium

<400> SEQUENCE: 23

Met Ser Ser Leu Phe Pro Thr Tyr Gln Arg Phe Asp Ile His Val Glu
1               5                   10                  15

Glu Ala Gln Gly Thr Lys Leu Ile Asp Asn Lys Gly Asn Glu Tyr Leu
            20                  25                  30

Asp Phe Ile Ser Gly Ile Ala Val Cys Asn Val Gly His Arg His Pro
        35                  40                  45

Asp Val Gln Lys Ala Val Glu Glu Gln Leu Asn Lys Val Trp His Val
    50                  55                  60

Ser Asn Leu Phe His Gln Ser Ile Gln Glu Asp Val Ala Gly Lys Leu
65                  70                  75                  80

Val Glu Arg Ser Asn Gly Asp Ala Val Phe Phe Cys Asn Ser Gly Ala
                85                  90                  95

Glu Ala Asn Glu Ala Ala Ile Lys Leu Ala Arg Lys Tyr Thr Gln Lys
            100                 105                 110

His Lys Ile Ile Thr Phe Thr Lys Ser Phe His Gly Arg Thr Phe Ala
        115                 120                 125

Thr Met Thr Ala Thr Gly Gln Ala Lys Ile His Asp Gly Phe Gly Pro
    130                 135                 140

Leu Val Asn Glu Phe Val Tyr Val Pro Tyr Asn Asp Glu Glu Ala Leu
145                 150                 155                 160

Lys Gln Glu Met Asp Asp Ser Val Ala Ala Ile Met Val Glu Val Ile
                165                 170                 175

Gln Gly Glu Gly Gly Val Val Pro Gly Thr Glu Ala Phe Leu Leu Thr
            180                 185                 190

Ile Gln Glu Leu Cys Lys Lys His Glu Ala Leu Phe Ile Val Asp Glu
```

```
        195                 200                 205

Val Gln Thr Gly Ile Gly Arg Thr Gly Lys Pro Phe Ala Tyr Gln His
    210                 215                 220

Phe Asn Val Ser Pro Asp Ile Ile Thr Ala Ala Lys Gly Leu Gly Ser
225                 230                 235                 240

Gly Met Pro Val Gly Ala Met Ile Gly Lys Gly Tyr Leu Lys Glu Ala
                245                 250                 255

Phe Gly Pro Gly Thr His Gly Thr Thr Phe Gly Gly Asn Pro Ile Ala
            260                 265                 270

Leu Ala Ser Ala Lys Ala Thr Leu Asn Ile Ile Phe Asn Glu Ala Phe
        275                 280                 285

Leu Ala Glu Val Thr Glu Lys Ser Leu Tyr Phe Thr Asn Ala Leu Lys
    290                 295                 300

Asn Ser Val Ala Asp Tyr Ser Phe Val Thr Asp Val Arg Gly Lys Gly
305                 310                 315                 320

Phe Met Ile Gly Ile Glu Cys Gly Glu His Gln Ser Ala Leu Leu Ala
                325                 330                 335

Ala Met Arg Glu Lys Gly Leu Leu Ala Leu Gly Ala Gly Pro His Val
            340                 345                 350

Val Arg Leu Leu Pro Pro Leu Thr Val Thr Lys Glu Glu Leu Asp Gln
        355                 360                 365

Ala Ile His Ile Ile Glu Glu Ala Phe Ser Gln Thr Lys Ile Thr Ser
    370                 375                 380


<210> SEQ ID NO 24
<211> LENGTH: 448
<212> TYPE: PRT
<213> ORGANISM: Burkholderia thailandensis MSMB121

<400> SEQUENCE: 24

Met Ser Thr His Ala Thr Asp Asp Trp Val Ala Arg Ser Leu Arg Ala
1               5                   10                  15

Val Trp His Pro Cys Thr Gln Met Lys His His Glu Arg Leu Pro Leu
            20                  25                  30

Ile Pro Val Ala Arg Gly Glu Arg Ala Trp Leu Phe Asp Arg Ala Gly
        35                  40                  45

Asn Arg Tyr Leu Asp Ala Ile Ser Ser Trp Trp Val Asn Leu Phe Gly
    50                  55                  60

His Ala Asn Pro Arg Ile Asn Ala Ala Leu Lys Gln Gln Leu Asp Thr
65                  70                  75                  80

Leu Glu His Ala Met Leu Ala Gly Cys Thr His Glu Ser Ala Ile Glu
                85                  90                  95

Leu Ala Glu Arg Leu Ala Ala Arg Thr Gln His Thr Leu Gly His Ala
            100                 105                 110

Phe Phe Ala Ser Asp Gly Ala Ser Ala Val Glu Ile Ala Leu Lys Met
        115                 120                 125

Ser Phe His Thr Trp Arg Asn Arg Gly Arg Gly Asp Lys Arg Glu Phe
    130                 135                 140

Val Cys Ile Ala Asn Gly Tyr His Gly Glu Thr Ile Gly Ala Leu Gly
145                 150                 155                 160

Val Thr Asp Val Ala Leu Phe Lys Asp Ala Tyr Asp Pro Leu Ile Arg
                165                 170                 175

Thr Ala His Val Val Ala Ser Pro Asp Ala Arg Gly Ala Arg Asp Gly
            180                 185                 190
```

```
Glu Thr Ala Ala Asp Val Ala Ala Arg Ala Leu Gly Asp Val Lys Arg
        195                 200                 205

Leu Phe Ala Glu Arg Gly Glu Lys Ile Ala Ala Leu Ile Val Glu Pro
    210                 215                 220

Leu Val Gln Cys Ala Ala Gly Phe Ala Met His Asp Pro Ser Tyr Val
225                 230                 235                 240

Arg Gly Val Arg Ala Leu Cys Asp Ala His Asp Val His Leu Ile Ala
                245                 250                 255

Asp Glu Ile Ala Val Gly Cys Gly Arg Thr Gly Thr Phe Phe Ala Cys
            260                 265                 270

Glu Gln Ala Ser Val Trp Pro Asp Phe Leu Cys Leu Ser Lys Gly Ile
        275                 280                 285

Ser Gly Gly Tyr Leu Pro Leu Ser Leu Val Leu Ser Arg Asp Ala Ile
    290                 295                 300

Phe Asp Ala Phe Tyr Asp Asp Asp Val Thr Arg Gly Phe Leu His Ser
305                 310                 315                 320

His Ser Tyr Thr Gly Asn Pro Leu Ala Cys Arg Ala Ala Val Ala Thr
                325                 330                 335

Leu Asp Leu Phe Asp Glu Asp Asp Val Leu Ala Glu Asn Ala Arg Lys
            340                 345                 350

Ala Ala Leu Met Arg Asp Ala Leu Ala Pro Leu Ala Ser His Pro Gln
        355                 360                 365

Val Arg His Leu Arg Glu Arg Gly Thr Ile Phe Ala Phe Asp Val Ala
    370                 375                 380

Leu Glu Gly Asp Ala Ala Gln Thr Phe Pro Arg Arg Phe Phe Gly His
385                 390                 395                 400

Ala Leu Thr Arg Glu Thr Leu Leu Arg Pro Ile Gly Thr Thr Val Tyr
                405                 410                 415

Leu Met Pro Pro Tyr Ile Leu Asp Asp Gly Glu Ile Glu Trp Leu Ala
            420                 425                 430

Ser Arg Thr Arg Ala Thr Leu Asp Ala Thr Leu Ser Glu Ala His Ala
        435                 440                 445


<210> SEQ ID NO 25
<211> LENGTH: 406
<212> TYPE: PRT
<213> ORGANISM: Klebsiella pneumoniae subsp. pneumoniae MGH 78578

<400> SEQUENCE: 25

Met Ala Thr Glu Gln Pro Ala Ile Thr Arg Ala Thr Phe Asp Glu Val
1               5                   10                  15

Ile Leu Pro Ile Tyr Ala Pro Ala Glu Phe Ile Pro Val Lys Gly Lys
            20                  25                  30

Gly Ser Arg Val Trp Asp Gln Gln Gly Lys Glu Tyr Ile Asp Phe Ala
        35                  40                  45

Gly Gly Ile Ala Val Thr Ala Leu Gly His Cys His Pro Ala Leu Val
    50                  55                  60

Ala Ala Leu His Gln Gln Gly Glu Thr Leu Trp His Thr Ser Asn Val
65                  70                  75                  80

Phe Thr Asn Glu Pro Ala Leu Arg Leu Gly Arg Lys Leu Val Glu Ala
                85                  90                  95

Thr Phe Ala Glu Arg Val Val Phe Met Asn Ser Gly Thr Glu Ala Asn
            100                 105                 110

Glu Thr Ala Phe Lys Leu Ala Arg His Tyr Ala Val Thr Arg His Ser
        115                 120                 125
```

```
Pro Tyr Lys Thr Lys Ile Ile Ala Phe His Asn Ala Phe His Gly Arg
    130                 135                 140

Ser Leu Phe Thr Val Ser Val Gly Gly Gln Pro Lys Tyr Ser Asp Gly
145                 150                 155                 160

Phe Gly Pro Lys Pro Ala Asp Ile Val His Val Pro Phe Asn Asp Leu
                165                 170                 175

Gln Ala Val Lys Ala Val Met Asp Asp His Thr Cys Ala Val Val Val
            180                 185                 190

Glu Pro Ile Gln Gly Glu Gly Gly Val Thr Ala Ala Thr Pro Ala Phe
        195                 200                 205

Leu Gln Gly Leu Arg Glu Leu Cys Asp Gln His Gln Ala Leu Leu Val
    210                 215                 220

Phe Asp Glu Val Gln Cys Gly Met Gly Arg Thr Gly Ser Leu Phe Ala
225                 230                 235                 240

Tyr Met His Tyr Gly Val Thr Pro Asp Ile Leu Thr Ser Ala Lys Ala
                245                 250                 255

Leu Gly Gly Gly Phe Pro Val Ser Ala Met Leu Thr Thr His Glu Ile
            260                 265                 270

Ala Ser Ala Phe His Ala Gly Ser His Gly Ser Thr Tyr Gly Gly Asn
        275                 280                 285

Pro Leu Ala Cys Ala Val Ala Asn Ala Ala Phe Asp Leu Ile Asn Thr
    290                 295                 300

Pro Ala Val Leu Asp Gly Val Ser Ala Lys Arg Glu Leu Phe Val Lys
305                 310                 315                 320

His Leu Gln Arg Leu Asp Ala Glu Phe Asp Leu Phe Ser Asp Ile Arg
                325                 330                 335

Gly Met Gly Leu Leu Ile Gly Ala Glu Leu Lys Pro Gln His Lys Gly
            340                 345                 350

Arg Ala Arg Asp Phe Leu Tyr Ala Ala Ala Asp Ala Gly Val Met Val
        355                 360                 365

Leu Asn Ala Gly Pro Asp Val Met Arg Phe Val Pro Ser Leu Ile Ile
    370                 375                 380

Asp Glu Gln Asp Ile Ala Glu Gly Met Ala Arg Phe Ala Gln Ala Val
385                 390                 395                 400

Ala Lys Val Ile Asn Gly
                405


<210> SEQ ID NO 26
<211> LENGTH: 288
<212> TYPE: PRT
<213> ORGANISM: Geobacillus toebii

<400> SEQUENCE: 26

Met Thr Leu Lys Leu Tyr Val Leu Thr Glu Lys Gln Phe Leu Pro Arg
1               5                   10                  15

His Glu Val Thr Tyr Pro Met Glu Glu Arg Gly Leu Gln Phe Gly Asp
            20                  25                  30

Gly Val Tyr Glu Val Ala Arg Ile Tyr Gln Gly Thr Tyr Phe Leu Leu
        35                  40                  45

Glu Glu His Ile Asp Arg Leu Tyr Arg Ser Ala Ala Ala Ile Arg Leu
    50                  55                  60

Ser Val Pro Phe Asp Lys Asp Val Leu Met Glu Lys Leu Glu Leu Leu
65                  70                  75                  80

Arg Glu Met Asn Asn Val Lys Glu Asp Ala Ile Leu Tyr Leu Gln Val
```

-continued

```
                85                  90                  95

Thr Arg Gly Ser Phe Pro Arg Asn His Ala Phe Pro Ala Glu Asn Arg
            100                 105                 110

Pro Asn Leu Tyr Ala Tyr Ile Arg Glu Met Pro Arg Lys Ile Arg Glu
        115                 120                 125

Ile Glu Asn Gly Val Arg Thr Ile Leu Thr Arg Asp Val Arg Trp Glu
    130                 135                 140

Tyr Cys Tyr Ile Lys Ser Leu Asn Leu Leu Pro Asn Val Leu Ala Lys
145                 150                 155                 160

Gln Glu Ala Thr Glu Arg Gly Ala Phe Glu Ala Ile Phe Tyr Arg Asp
                165                 170                 175

Gly Asp Ile Thr Glu Gly Ser Ser Ser Asn Ile Phe Leu Val Lys Asp
            180                 185                 190

Gly Lys Val Tyr Thr His Pro Ala Thr Glu Arg Ile Leu Asn Gly Ile
        195                 200                 205

Ile Arg Met Lys Val Lys Glu Phe Cys Asp Leu Phe His Ile Pro Phe
    210                 215                 220

Val Glu Glu Ala Phe Ser Ile Glu Asp Ile Ala Gln Ala Asp Glu Met
225                 230                 235                 240

Phe Leu Thr Ser Thr Thr Ser Ser Ile Ile Pro Ile Ile Gln Val Glu
                245                 250                 255

Glu Gln Leu Ile Ala Asp Gly Lys Pro Gly Glu Val Thr Arg Lys Leu
            260                 265                 270

Gln Ala Ala Tyr Glu Lys Ala Ala Gly Leu Ala Val Lys Asn Ala Lys
        275                 280                 285


<210> SEQ ID NO 27
<211> LENGTH: 327
<212> TYPE: PRT
<213> ORGANISM: Talaromyces cellulolyticus

<400> SEQUENCE: 27

Met Ala Thr Met Asp Gln Ile Phe Ala Gly Tyr Arg Asp Arg Met Asn
1               5                   10                  15

Asp Leu Glu Ala Thr Tyr Asp Lys Ser Pro Phe Ala Arg Gly Val Ala
            20                  25                  30

Trp Ile Glu Gly Asp Leu Val Pro Ile Asp Lys Ala Ser Ile Pro Leu
        35                  40                  45

Leu Asp Gln Gly Phe Met His Ser Asp Leu Thr Tyr Asp Val Pro Ser
    50                  55                  60

Val Trp Asp Gly Arg Phe Phe Arg Leu Asp Asp His Leu Thr Arg Leu
65                  70                  75                  80

Gln Thr Asn Cys Lys Lys Met Arg Leu Gln Leu Pro Leu Pro Glu Glu
                85                  90                  95

Glu Val Lys Lys Ile Leu Ile Glu Ile Val Ala Lys Ser Gly Ile Arg
            100                 105                 110

Asp Ala Phe Val Gln Leu Ile Val Thr Arg Gly Leu Lys Ser Val Arg
        115                 120                 125

Gly Ala Val Pro Cys Glu Val Leu Lys Asn Asn Leu Tyr Met Phe Val
    130                 135                 140

Gln Pro Phe Val Trp Val Met Glu Pro Glu Met Gln Leu Thr Gly Gly
145                 150                 155                 160

Lys Ala Val Val Ala Arg Thr Val Lys Arg Thr Pro Ser Asp Cys Phe
                165                 170                 175
```

-continued

```
Asp Pro Thr Ile Lys Asn Leu Gln Trp Gly Asp Leu Thr Arg Gly Met
            180                 185                 190

Phe Glu Ala Ala Asp Arg Ser Ala Met Tyr Pro Phe Leu Thr Asp Gly
        195                 200                 205

Asp Gly Asn Leu Thr Glu Gly Ser Gly Phe Asn Val Val Leu Val Lys
    210                 215                 220

Asp Gly Val Leu Tyr Thr Pro Asp Arg Gly Val Leu Pro Gly Ile Thr
225                 230                 235                 240

Arg Lys Ser Val Val Asp Val Ala Lys Ser Leu Ser Leu Glu Val Arg
                245                 250                 255

Val Glu Asp Val Pro Thr Glu Met Ala Tyr Asn Cys Asp Glu Ile Phe
            260                 265                 270

Met Cys Thr Thr Ala Gly Gly Ile Met Pro Ile Thr Glu Leu Asp Gly
        275                 280                 285

Lys Pro Val Lys Asp Gly Asn Ile Gly Ala Ile Thr Lys Gln Ile Trp
    290                 295                 300

Asp Gly Tyr Trp Ala Leu His Tyr Asp Pro Ser Tyr Thr Phe Glu Ile
305                 310                 315                 320

Asp Tyr Ala Thr Gly Ala Ala
                325
```